US010508271B2

(12) United States Patent
Jenkinson et al.

(10) Patent No.: US 10,508,271 B2
(45) Date of Patent: Dec. 17, 2019

(54) TARGETED MUTATIONS

(71) Applicant: GREEN BIOLOGICS LIMITED, Abingdon, Oxfordshire (GB)

(72) Inventors: Elizabeth Jenkinson, Abingdon (GB); Preben Krabben, Didcot (GB)

(73) Assignee: GREEN BIOLOGICS LIMITED, Abingdon, Oxfordshire (GB)

( * ) Notice: Subject to any disclaimer, the term of this patent is extended or adjusted under 35 U.S.C. 154(b) by 210 days.

(21) Appl. No.: 15/304,483

(22) PCT Filed: Apr. 16, 2015

(86) PCT No.: PCT/GB2015/051153
§ 371 (c)(1),
(2) Date: Jan. 3, 2017

(87) PCT Pub. No.: WO2015/159087
PCT Pub. Date: Oct. 22, 2015

(65) Prior Publication Data
US 2017/0037393 A1    Feb. 9, 2017

(30) Foreign Application Priority Data
Apr. 17, 2014  (GB) .................................. 1406970.2

(51) Int. Cl.
C12N 15/10    (2006.01)
C12N 15/90    (2006.01)
C12N 15/74    (2006.01)

(52) U.S. Cl.
CPC .......... *C12N 15/102* (2013.01); *C12N 15/74* (2013.01); *C12N 15/902* (2013.01); *C12N 2830/00* (2013.01)

(58) Field of Classification Search
None
See application file for complete search history.

(56) References Cited

U.S. PATENT DOCUMENTS

| 8,420,782 B2 | 4/2013 | Bonas et al. |
| 2011/0027835 A1 | 2/2011 | Heap et al. |
| 2011/0119779 A1 | 5/2011 | Shizuya et al. |
| 2012/0190116 A1 | 7/2012 | Soucaille et al. |
| 2012/0202251 A1 | 8/2012 | Cornish et al. |
| 2012/0301964 A1 | 11/2012 | Tracy et al. |
| 2014/0141516 A1 | 5/2014 | Tracy et al. |

FOREIGN PATENT DOCUMENTS

| NO | 2002/0047 | 7/2003 |
| WO | WO 2003/056936 | 7/2003 |
| WO | WO 2007/148091 | 12/2007 |
| WO | WO 2008/040387 | 4/2008 |
| WO | WO 2009/101400 | 8/2009 |
| WO | WO 2013/133882 | 9/2013 |
| WO | WO 2013/141680 | 9/2013 |
| WO | WO 2013/142578 | 9/2013 |
| WO | WO 2014/093595 | 6/2014 |
| WO | WO 2014/143381 | 9/2014 |
| WO | WO 2014/191518 | 12/2014 |
| WO | WO 2015/040402 | 3/2015 |
| WO | WO 2015/123339 | 8/2015 |

OTHER PUBLICATIONS

Al-Hinai, M., Fast, A. and Papoutsakis, E. (2012) 'Novel system for efficient isolation of Clostridium double-crossover allelic exchange mutants enabling markerless chromosomal gene deletions and DNA integration', Applied and environmental microbiology, 78(22), pp. 8112-8121.
Altschul, S., Madden, T., Schäffer, A., Zhang, J., Miller, W. and Lipman, D. (1997) 'Gapped BLAST and PSI-BLAST: A new generation of protein database search programs', Nucleic acids research, 25(17), pp. 3389-3402.
Bahl, H. and Dürre, P. (eds.) (2001) Clostridia: Biotechnology and Medical Applications. Wiley-Blackwell.
Barrangou, R. and Marraffini, L. (2014) 'CRISPR-Cas systems: Prokaryotes upgrade to adaptive immunity', Molecular cell., 54(2), pp. 234-244.
Brown, S., Nagaraju, S., Utturkar, S., Tissera, D., Segovia, S., Mitchell, W., Land, M., Dassanayake, A. and Köpke, M. (2014) 'Comparison of single-molecule sequencing and hybrid approaches for finishing the genome of Clostridium autoethanogenum and analysis of CRISPR systems in industrial relevant Clostridia', Biotechnology for biofuels, 7.
Cartman, S., Kelly, M., Heeg, D., Heap, J. and Minton, N. (2012) 'Precise manipulation of the Clostridium difficile chromosome reveals a lack of association between the tcdC genotype and toxin production', Applied and environmental microbiology, 78(13), pp. 4683-4690.
Cobb, R., Wang, Y. and Zhao, H. (2014) 'High-efficiency multiplex genome editing of Streptomyces species using an engineered CRISPR/Cas system', ACS synthetic biology, 4(6), pp. 723-8.
Cong, L., Ran, F., Cox, D., Lin, S., Barretto, R., Habib, N., Hsu, P., Wu, X., Jiang, W., Marraffini, L. and Zhang, F. (2013) 'Multiplex genome engineering using CRISPR/Cas systems' and Supplementary Materials, Science (New York, N.Y.)., 339(6121), pp. 819-823.
Constantino PNAS 100,15748-15753 (2003).
DiCarlo, J., Norville, J., Mali, P., Rios, X., Aach, J. and Church, G. (2013) 'Genome engineering in *Saccharomyces cerevisiae* using CRISPR-Cas systems', Nucleic acids research., 41(7), pp. 4336-4343.

(Continued)

*Primary Examiner* — Nancy A Treptow
(74) *Attorney, Agent, or Firm* — Knobbe Martens Olson & Bear LLP

(57) ABSTRACT

The present invention relates to a process for producing and selecting for targeted mutations in bacterial genomes. In particular, the process relates to the transformation of bacteria with a Recombination Element which comprises the desired mutation followed by homologous recombination of the Recombination Element into the bacterial genome; the CRISPR/Cas system is then used to eliminate bacteria which do not have the desired mutation.

14 Claims, 7 Drawing Sheets
Specification includes a Sequence Listing.

(56) References Cited

OTHER PUBLICATIONS

Didelot, X. and Falush, D. (2007) 'Inference of bacterial Microevolution using Multilocus sequence data', Genetics, 175(3).
Doudna, J. and Charpentier, E. (2014) 'Genome editing. The new frontier of genome engineering with CRISPR-Cas9', Science (New York, N.Y.), 346(6213).
Fujii, W., Onuma, A., Sugiura, K. and Naito, K. (2014) 'Efficient generation of genome-modified mice via offset-nicking by CRISPR/Cas system', Biochemical and biophysical research communications., 445(4), pp. 791-4.
Garneau, J.E., Dupuis, M.E., Villion, M., Romero, D.A., Barrangou, R., Boyaval, P., Fremaux, C., Horvath, P., Magadan, A.H. and Moineau, S. (2010) 'The CRISPR/Cas bacterial immune system cleaves bacteriophage and plasmid DNA', Nature, 468(7320), pp. 67-71. doi: 10.1038/nature09523.
Gomaa, A.A., Klumpe, H.E., Luo, M.L., Selle, K. and Barrangou, R. (2014) 'Programmable removal of bacterial strains by use of genome-targeting CRISPR-Cas systems', mBio, 5(1), pp. 13-928. doi: 10.1128/mBio.00928-13.
Gratz, S., Wildonger, J., Harrison, M. and O'Connor-Giles, K. (2013) 'CRISPR/Cas9-mediated genome engineering and the promise of designer flies on demand', Fly., 7(4), pp. 249-255.
Grissa, I., Vergnaud, G. and Pourcel, C. (2007) 'CRISPRFinder: A web tool to identify clustered regularly interspaced short palindromic repeats', Nucleic acids research, 35.
Heap, J.T., Cartman, S.T., Pennington, O.J., Cooksley, C.M., Scott, J.C., Blount, B., Burns, D. and Minton, N.P. (2009) 'Development of Genetic Knock-out Systems for Clostridia', in Bruggemann, H. and Gottschalk, G. (eds.) Clostridia: Molecular biology in the Post-genomic Era.
Heap, J.T., Pennington, O.J., Cartman, S.T. and Minton, N.P. (2009) 'A modular system for Clostridium shuttle plasmids', Journal of Microbiological Methods, 78(1), pp. 79-85. doi: 10.1016/j.mimet.2009.05.004.
Horii, T., Morita, S., Kimura, M., Kobayashi, R., Tamura, D., Takahashi, R., Kimura, H., Suetake, I., Ohata, H., Okamoto, K., Tajima, S., Ochiya, T., Abe, Y. and Hatada, I. (2013) 'Genome engineering of mammalian haploid embryonic stem cells using the Cas9/RNA system', PeerJ, 1.
Hwang, W.Y., Fu, Y., Reyon, D., Maeder, M.L., Tsai, S.Q., Sander, J.D., Peterson, R.T., Yeh, J.J. and Joung, K.J. (2013) 'Efficient in vivo genome editing using RNA-Guided Nucleases', Nature Biotechnology, 31(3).
Jiang, W., Bikard, D., Cox, D., Zhang, F. and Marraffini, L. (2013) 'RNA-guided editing of bacterial genomes using CRISPR-Cas systems' and Supplementary Materials, Nature biotechnology, 31(3), pp. 233-9.
Hiro, R., Shitrit, D. and Qimron, U. (2014) 'Efficient engineering of a bacteriophage genome using the type I-E CRISPR-Cas system', RNA biology, 11(1), pp. 42-44.
Lee, J., Jang, Y., Lee, J., Papoutsakis, E. and Lee, S. (2009) 'Metabolic engineering of Clostridium acetobutylicum M5 for highly selective butanol production', Biotechnology journal, 4(10), pp. 1432-1440.
Ma, B., Tromp, J. and Li, M. (2002) 'PatternHunter: Faster and more sensitive homology search', Bioinformatics (Oxford, England), 18(3), pp. 440-5.
Maiden, M., Bygraves, J., Feil, E., Morelli, G., Russell, J., Urwin, R., Zhang, Q., Zhou, K., Caugant, D., Feavers, I., Achtman, M. and Spratt, B. (1998) 'Multilocus sequence typing: A portable approach to the identification of clones within populations of pathogenic microorganisms', Proceedings of the National Academy of Sciences of the United States of America, 95(6), pp. 3140-5.
Makarova, K., Haft, D., Barrangou, R., Brouns, S., Charpentier, E., Horvath, P., Moineau, S., Mojica, F., Wolf, Y., Yakunin, A., der, van and Koonin, E. (2011) 'Evolution and classification of the CRISPR-Cas systems', Nature reviews Microbiology, 9(6), pp. 467-477.

Mali, P., Yang, L., Esvelt, K., Aach, J., Guell, M., DiCarlo, J., Norville, J. and Church, G. (2013) 'RNA-guided human genome engineering via Cas9', Science (New York, N.Y.), 339(6121), pp. 823-6.
Nair, R.V. and Papoutsakis, E.T. (1994) 'Expression of plasmid-encoded aad in Clostridium acetobutylicum M5 restores vigorous butanol production', Journal of Bacteriology, 176(18), pp. 5843-5846. doi: 10.1128/jb.176.18.5843-5846.1994.
Ran, F.A., Hsu, P.D., Wright, J., Agarwala, V., Scott, D.A. and Zhang, F. (2013) 'Genome engineering using the CRISPR-Cas9 system', Nature Protocols, 8(11), pp. 2281-2308. doi: 10.1038/nprot.2013.143.
Ran, F., Hsu, P., Lin, C., Gootenberg, J., Konermann, S., Trevino, A., Scott, D., Inoue, A., Matoba, S. and Zhang, Y. (2013) 'Double nicking by RNA-guided CRISPR Cas9 for enhanced genome editing specificity', Cell., 154(6), pp. 1380-9.
Richter, H., Randau, L. and Plagens, A. (2013) 'Exploiting CRISPR/Cas: Interference mechanisms and applications', International Journal of Molecular Sciences, 14(7).
Richter, H., Zoephel, J., Schermuly, J., Maticzka, D., Backofen, R. and Randau, L. (2012) 'Characterization of CRISPR RNA processing in Clostridium thermocellum and Methanococcus maripaludis', Nucleic acids research., 40(19), pp. 9887-9896.
Rocha, E.P.C., Cornet, E. and Michel, B. (2005) 'Comparative and evolutionary analysis of the bacterial homologous recombination systems', PLoS Genetics, 1(2).
Sillers, R., Chow, A., Tracy, B. and Papoutsakis, E. (2008) 'Metabolic engineering of the non-sporulating, non-solventogenic Clostridium acetobutylicum strain M5 to produce butanol without acetone demonstrate the robustness of the acid-formation pathways and the importance of the electron balance', Metabolic engineering, 10(6), pp. 321-332.
Upadhyay, S., Kumar, J., Alok, A. and Tuli, R. (2013) 'RNA-guided genome editing for target gene mutations in wheat', G3 (Bethesda, Md.), 3(12), pp. 2233-8.
Vercoe, R., Chang, J., Dy, R., Taylor, C., Gristwood, T., Clulow, J., Richter, C., Przybilski, R., Pitman, A. and Fineran, P. (2013) 'Cytotoxic chromosomal targeting by CRISPR/Cas systems can reshape bacterial genomes and expel or remodel pathogenicity islands', PLoS genetics, 9(4).
Vos, M. and Didelot, X. (2008) 'A comparison of homologous recombination rates in bacteria and archaea', The ISME journal, 3(2), pp. 199-208.
Wang, Y., Zhang, Z., Seo, S., Choi, K., Lu, T., Jin, Y. and Blaschek, H. (2015) 'Markerless chromosomal gene deletion in Clostridium beijerinckii using CRISPR/Cas9 system', Journal of biotechnology, 200, pp. 1-5.
Westra, E., Staals, R., Gort, G., Høgh, S., Neumann, S., de, la, Fineran, P. and Brouns, S. (2013) 'CRISPR-Cas systems preferentially target the leading regions of MOBF conjugative plasmids', RNA biology, 10(5), pp. 749-761.
Xu, T., Li, Y., Shi, Z., Hemme, C., Zhu, Y., Nostrand, V., He, Z. and Zhou, J. (2015) 'Efficient genome editing in Clostridium cellulolyticum via CRISPR-Cas9 Nickase' and Supplementary Materials, Applied and environmental microbiology, 81(13), pp. 4423-4431.
Zhong, J., Karberg, M. and Lambowitz, A. (2003) 'Targeted and random bacterial gene disruption using a group II intron (targetron) vector containing a retrotransposition-activated selectable marker', Nucleic acids research, 31(6), pp. 1656-1664.
Li et al., CRISPR/Cas: A novel way of RNA-guided genome editing, Chinese Academy of Sciences, Beijing, China, 2013, 35(11): 1265-1273.
Sontheimer et al., Microbiology: Slicer for DNA, Nature, 2010, 468(732): 45-56.
Combined Search and Examination Report dated Feb. 1, 2016 for Application No. GB1506469.4.
Examination Report dated Aug. 1, 2016 for Application No. GB1506469.4.
Combined Search and Examination Report dated Nov. 1, 2016 for Application No. GB1616433.7.
Combined Search and Examination Report dated Nov. 1, 2016 UK Application No. GB1616429.5.

(56) References Cited

OTHER PUBLICATIONS

Official Letter dated Sep. 18, 2017 for EP Application No. 15718987.9.
Official Letter dated Jul. 26, 2018 for EP Application No. 15718987.9.
Office Action dated Sep. 7, 2018 for U.S. Appl. No. 15/304,467.
Combined Search and Examination Report dated Feb. 1, 2016 for Application No. GB1506460.3.
Examination Report dated Jul. 1, 2016 for Application No. GB1506460.3.
Official Letter dated Sep. 14, 2017 for EP Application No. 15718988.7.
Official Letter dated Jul. 26, 2018 for EP Application No. 15718988.7.
International Search Report and Written Opinion dated Jun. 26, 2015 for International Application No. PCT/GB2015/051153.
International Search Report and Written Opinion dated Jun. 26, 2015 for International Application No. PCT/GB2015/051152.
Office Action issued in related Chinese patent application No. 201580024688X dated Jan. 9, 2019.
Office Action issued in related Chinese patent application No. 2015800246907 dated Jan. 15, 2019.
JP Official Action dated Apr. 23, 2019 for application No. 2017-505733 with machine translation thereof.
US Official Action dated Mar. 21, 2019 for application No. 15/304,467.
Office Action issued in CN Application No. 2015800246907 dated May 24, 2019.

Figure 2

| SEQ ID NO: | | |
|---|---|---|
| 6. | C_saccharoper_N1504 | CTTTTAATATATCCATATTGGAATGTAAAT |
| 7. | C_saccharoper_N14_HMT | GTTTTATATTAAC-TATGAGGAATGTAAAT |
| 8. | C_sp_DLVIII | GTTTTATATTAAC-TATGAGGAATGTAAAT |
| 9. | C_saccharob_NCP258_2 | GTTTTATCTTAAC-TA-GAGGAATGTAAAT |
| 10. | C_tyro_ATCC52755_1 | GTTGAACCTTAACATGAGATGTATTTAAAT |
| 11. | C_tyro_ATCC52755_2 | ATTGAACCTTAACATGAGATGTATTTAAAT |
| 12. | C_saccharob_NCP262_1 | GATTAACATTAACATGAGATGTATTTAAAT |
| 13. | C_saccharob_NCP258_1 | GTTGAAGATTAACATTATATGTTTTGAAAT |
| 14. | C_saccharob_NCP262_2 | GTTGAAGATTAACATTATATGTTTTGAAAT |
| 15. | C_pasteurianum_DSM525 | GTTGAACCTTAACATAGGATGTATTTAAAT |
| 16. | C_autoethanogenum | GTTGAACCTCAACATGAGATGTATTTAAAT |

Figure 5

```
WT                          tgttagaaagtgaagtatctaaacaaattacaactccactgctgctccagcgtttcctagggggaccatatagatttcat
Expected mutations
Control sequence – 1        tgttagaaagtgaagtatctaaacaaattacaactcTactgctgctccagcgtttccAagAggaccatatagatttcat
  mutation
Col A                       TGTTAGAAAGTGAAGTATCTAAACAAATTACAACTCTACTTGCTGCTCCAGCGTTTCCTAGGGACCATATAGATTTCAT
Col B                       TGTTAGAAAGTGAAGTATCTAAACAAATTACAACTCTACTTGCTGCTCCAGCGTTTCCAAGAGGACCATATAGATTTCAT
Col B                       TGTTAGAAAGTGAAGTATCTAAACAAATTACAACTCTACTTGCTGCTCCAGCGTTTCCAAGAGGACCATATAGATTTCAT
```

Mutated PAM site
WT = CCA
Mutants = CTA

Deleted AvrII site
WT = CCTAGG
Mutants = CCAAGA

WT = SEQ ID NO: 17
Control = SEQ ID NO: 18
Mutation = SEQ ID NO: 19
Col A/Col B = SEQ ID NO: 20

TARGETED MUTATIONS

The present invention relates to a process for producing and selecting for targeted mutations in bacterial genomes. In particular, the process relates to the transformation of bacteria with a Recombination Element which comprises the desired mutation followed by homologous recombination of the Recombination Element into the bacterial genome; the CRISPR/Cas system is then used to eliminate bacteria which do not have the desired mutation.

Solvent-producing clostridia were first used during the 1920s and 1930s for the industrial production of acetone, butanol and ethanol. During the 1950s, the establishment of more efficient petrochemical techniques to synthesise these solvents lead to the abandonment of such large-scale bacterial fermentations. However, in the present environment, with increasing pressure for the development of chemicals using sustainable and renewable processes, the interest in clostridial fermentations for the production of solvents is being renewed. This has also been helped by advancements in the biological understanding of these solventogenic clostridia, with the sequencing of several genomes and the use of RNA sequencing and transcriptomics. These areas of research have opened up the possibility of engineering new strains capable of over-producing butanol, or removing production of competing by-products, further improving the economics of solventogenic fermentations.

In order to take advantage of this influx of genomic information, there remains a need for quick and reliable methods of generating commercially-relevant recombinant clostridial strains and other bacterial strains.

It has been traditionally very difficult to generate recombinant clostridial strains. Low transformation efficiencies in combination with low recombination efficiencies have hampered efforts to make stable recombinant strains exhibiting improved solvent-related phenotypes. Over the past few years, technology has been developed that allows insertional inactivation of genes through use of Type II introns, e.g. Targetron (Sigma) and Clostron (e.g. WO 2007/148091), and integration of new pathway genes through the use of 'allele coupled exchange' (ACE, e.g. WO 2009/101400), but introduction of multiple mutations is difficult and very little work has been done on the introduction of specific base changes (single nucleotide polymorphisms, SNPs). Current technology is not good enough to achieve either of these aims routinely.

Early work on clostridial genetic systems resulted in strains carrying single crossovers to generate strains carrying mutations in specific genes but these are not precise, they are genetically unstable and leave plasmid and antibiotic marker genes in the cell. They can also potentially have polar effects (e.g. they may affect other genes), especially if the gene targeted is operonic.

Making recombinant strains of, e.g. *E. coli*, can be accomplished through transformation with linear DNA (but the required recombination only works efficiently in recombineering strains, e.g. *E. coli* HME63 as used by Jiang et al. 2013, infra) or suicide vectors but in clostridia these methods are not applicable because the low recombination frequencies do not allow for recombination events to occur before DNA is lost from the cell. In order to overcome this, many methods employ the use of stable replicative vectors but then these, after the recombination event, have to be lost from the cell, otherwise antibiotic and other marker genes are left behind, preventing further manipulation. Plasmids can be lost by using temperature sensitive replicons; pseudo-suicide vectors (these carry Origins that exhibit unstable segregation and can eventually be lost from the population) (e.g. Heap et al., J. Microbiol. Methods, 78(1), 79-85. 2009); introduction of restriction enzyme sites into the recombination vector; and cloning a restriction endonuclease (or use of genomic copy of restriction endonuclease) under an inducible promoter. Alternatively FLP/FRT recombinase can be used to remove selectable markers and other selected regions of the plasmid after integration (e.g. WO 2008/040387). However these methods add extra steps and increase complexity to the system.

A number of publications have demonstrated deletion of specific genes in clostridia through either insertion of an antibiotic resistance cassette (e.g. Clostron) or in-frame using homologous recombination coupled with counter-selection. This is dependent on counter-selection gene homologues located on the chromosome (e.g. pyrE) or introduced heterogeneously (e.g. codA from *E. coli*). To date, there is very little evidence of clostridial strains engineered to carry specific SNPs. Some work has been done in *C. difficile* (e.g. Cartman et al., Appl. Environ. Micro. (2012) July; 78(13):4683-90) but the use of counter-selection markers results in the requirement for marker gene homologues to be cloned into plasmids, selection using chemicals that are toxic if the cell is still carrying the gene homologue (i.e. to select for double crossover events), and then screening for the desired genetic change because the method does not distinguish between WT (wild-type) revertants and cells incorporating mutations. If the resulting recombinant strain still carries the PyrE deletion then additional steps must be taken to repair the strain.

Some counter-selection methods require a deletion strain to be created before the method can be used (e.g. ACE) and there is a risk of introducing additional unwanted mutations through the use of toxic analogues as the counter-selection. For example, pyrE mutants are often used to generate recombinant strains. These mutants are able to grow on 5-fluoroorotic acid (5-FOA), whereas cells with a wild type pyrE gene convert 5-FOA to a toxic analogue causing cell death. However, pyrE is part of the uracil biosynthesis pathway and so these mutants also require the addition of uracil to the media for growth. Interfering in nucleotide biosynthesis pathways such as these may also have unexpected and unwanted additional effects.

RNA knock-down and interference methods can be useful for research purposes but are not suitable for construction of commercial solventogenic clostridial strains. Transposon mutagenesis is also a valuable tool for generating recombinant strains but, like chemical mutagenesis, cannot be targeted to a specific genomic location, thereby making it a valuable research tool rather than a viable method for constructing industrially-relevant clostridial strains.

A new method which could potentially be used to make precise genome changes is Transcriptional Activator-Like Endonucleases (TALENs, e.g. U.S. Pat. No. 8,420,782 B2) but the technology has been developed for editing eukaryotic genomes and has not yet been specifically adapted for use in industrially-relevant solventogenic clostridial strains. The need to engineer TALENs for each gene target is costly and time-consuming, and the practicalities of precisely how the technology will work in clostridia all count against it becoming a widely accessible tool in the near future.

There remains a need therefore for a versatile method for genetic manipulation that will overcome the multiple challenges encountered when using currently available tools for clostridia namely: low transformation frequencies, low recombination efficiencies, inability to select for gene replacement strains over WT revertants, unwanted polar effects, unwanted additional mutations that can occur when using toxic analogues for counter-selection steps (and the need to use deletion strains rather than WT for some of these methods), difficulties in making multiple layered mutations, and the need to ensure loss of the recombination vector after the double crossover event.

A novel method has therefore been developed which is based on using the clostridial CRISPR/Cas system. (CRISPR is an acronym for Clustered, Regularly Interspaced, Short, Palindromic Repeats.) These systems are usually described as 'prokaryotic adaptive immune systems' and are the means by which a bacterial or archaeal cell can protect itself from invading DNA, usually phage or plasmid DNA.

Cells with a CRISPR/Cas system are able to selectively integrate short fragments from 'invading' DNA into the Cas gene cluster. Each fragment is called a 'Spacer' and is flanked by direct repeats. If the cell encounters the same invading DNA again, it will recognise it as hostile and will destroy it by cleaving it with the Cas endonuclease.

The sequence that the CRISPR/Cas system recognises in the invading DNA is called the Protospacer' and has identity to the Spacer copy in the genome. In order to make sure that the cell does not accidently attack the genomic copy of the Spacer, the Protospacer in Cas I or Cas II systems must have a short sequence associated with it called the PAM sequence. The PAM sequence may be up- or down-stream of the Protospacer sequence depending on the type of system. If it is not present or is mutated in any way, the invading DNA will no longer be recognised by the cell and it will not be destroyed.

The PAM sequence associated with cas9 from *Streptococcus pyogenes* is well known (Jiang et al., Nature Biotech. (March 2013), vol. 31, no. 3, pp. 233-239); however, the PAM sequence associated with clostridial systems has not previously been identified.

Not all prokaryotes have CRISPR/Cas gene homologues and of those that do they fall into several distinct classes (Makarova et al., Nat. Rev. Microbiol., 9(6), 467-77. 2011). A lot of work has been published on the Type II cas 9 system from *Streptococcus pyogenes* and *Streptococcus pneumoniae* (e.g. Jiang et al., Nature Biotech. (March 2013), vol. 31, no. 3, pp. 233-239). This has been developed into a genome-editing tool for use in eukaryotic cells, which has been used successfully in e.g. yeast (DiCarlo et al., Nucleic Acids Research, 41(7), 4336-4343, 2013), zebrafish (Hwang et al., Nat. Biotechnol., 31(3), 227-9. 2013) and mammalian cells (Ran et al., Nature Protocols, 8, 2281-2308, 2013).

Many excellent molecular tools have been developed for use with well-studied bacteria such as *E. coli*. These tools include suites of different plasmids and highly efficient transformation and recombineering techniques. However, many of these tools are not applicable to bacteria such as Clostridia. For example, Soucaille et al. (US 2012/0190116) note that classic techniques used in *E. coli* based on the utilisation of linear DNA are not feasible in Clostridia due to the short intracellular and extracellular half-life of the linear fragments, degradation by clostridial DNAses and DNA restriction endonucleases.

Patent applications from Tracy & Papoutsakis (e.g. US 2012/0301964 A1, and US 2014/0141516 A1) state that a comparative genomics study by Rocha et al. (PLoS Genet., 2005. 1(2): p. e15) of the essential homologous recombination machinery indicates that Clostridia lack any obvious resolvase gene to catalyze the intramolecular resolution reaction between heteroduplexes of recombination intermediates. To overcome this they added non-endogenous resolvase activity by expression of a recU gene from *B. subtilis* in *Clostridium acetobutylicum*. However, recombinogenic strains are genetically unstable and are therefore not suitable for future commercial use.

A new process has now been developed which enables the production of desired mutations in bacterial genomes in a quick and efficient manner, without the need to supplement the bacteria with enzymes to enhance recombination efficiency. In this process, low transformation and recombination efficiencies become largely irrelevant. By directing a 'Killing Vector' to unmutated target sequences, cells carrying the unmutated sequences can be targeted and killed, thereby ensuring that the only recovered cells are those carrying the desired mutation; no screening is required. As this is a very precise process, polar effects (which are often seen using more crude methods) can be eliminated. Additionally, counter-selection markers are not required, therefore eliminating the need to use deletion strains and removing the possibility of inadvertently producing unwanted mutations through the use of toxic analogues for selection.

In this new process, DNA changes are permanent and stable; and the removal (or loss) of the transformed vectors means that multiple layers of mutations can easily be made. The process also facilitates the targeting of more than one gene or DNA element at a time, thus allowing several genetic modifications to be made at one time.

In one embodiment, therefore, the invention provides a process for producing a mutation in an Intended Mutagenesis Region (IMR) within a bacterial genome, wherein the bacteria comprise a CRISPR/Cas system, and wherein the IMR comprises a CRISPR PAM/Protospacer which is capable of being recognised by the bacteria's CRISPR/Cas systems, the process comprising the steps:

(a) transforming a population of said bacteria with a Recombination Vector, wherein the Recombination Vector comprises a Recombination Element, wherein the Recombination Element comprises:
  (i) a Substitution Element, wherein the Substitution Element comprises the mutation, and
  (ii) Homology Arms which flank the Substitution Element, wherein the Homology Arms are capable of promoting the replacement of all or part of the IMR in the bacterial genome with an element which comprises the Substitution Element, wherein the Recombination Element does not comprise a CRISPR PAM/Protospacer which is capable of being recognised by a crRNA which recognises the CRISPR/PAM Protospacer in the IMR;

(b) culturing the population of bacteria under conditions wherein, in one or more bacteria within the population, all or part of the IMR in the genomes of those bacteria is replaced by an element which comprises the Substitution Element and whereby the CRISPR PAM/Protospacer is removed from the IMR in the genomes of those bacteria or is rendered incapable of being recognised by a crRNA which recognises the CRISPR/PAM Protospacer in the IMR;

(c) transforming the population of bacteria with a Killing Vector which is capable of directing production of a crRNA which targets the CRISPR PAM/Protospacer in the IMR of any bacteria in the population from which the CRISPR PAM/Protospacer has not been removed or rendered incapable of being recognised by the crRNA, thereby promoting the CAS endonuclease-induced cleavage of those CRISPR PAM/Protospacers which are recognised by the crRNA and the subsequent death of those bacteria; and (d) selecting or isolating one or more bacteria from the population whose genomes comprise the Substitution Element comprising the mutation.

The IMR (Intended Mutagenesis Region) is the DNA sequence in the bacterial genome within which it is intended to make the desired mutation.

In some embodiments of the invention, the IMR corresponds to the region in the bacterial genome whose 5'-end corresponds to the upstream end of the 5'-Homology Arm of the Recombination Element and whose 3'-end corresponds to the downstream end of the 3'-Homology Arm of the Recombination Element.

As used herein, the term "bacterial genome" or "genomic DNA" refers primarily to the circular bacterial chromosome, but the term may also encompass endogenous plasmids (e.g. a clostridial megaplasmid, or smaller endogenous plasmids) which are essential to the viability of the bacteria, optionally under certain conditions, or which may be selected for under defined conditions. For example, these endogenous plasmids could confer the ability to grow in the presence of an otherwise toxic substance (e.g. antibiotic or heavy metal) or competing microorganism, or to utilise specific substrates for growth. In embodiments of the invention wherein the bacterial genome or genomic DNA to be mutated is such an endogenous plasmid, the process optionally includes the step of culturing the population of bacteria under conditions which select for the presence of the plasmid.

The bacteria in the population of bacteria must have a CRISPR/Cas system. This CRISPR/Cas system will be one which is capable of cleaving the genomes of bacteria within the population which still comprise the PAM/Protospacer when those bacteria are transformed with the Killing Vector.

It will be accepted that there may, in some cases, be contamination within bacterial populations. As used herein, the term "population of bacteria" refers primarily to the bacteria which it is desired to transform with the Recombination Vector and the Killing Vector.

Preferably, the CRISPR/Cas system is a Type I CRISPR/Cas system.

The bacteria in the population may have an endogenous CRISPR/Cas system or the CRISPR/Cas system may be heterologous. For example, a heterologous CRISPR/Cas system may be plasmid-based.

Preferably, the CRISPR/Cas system is an endogenous CRISPR/Cas system, i.e. it is present in the wild-type bacteria. In some embodiments of the invention, the CRISPR/Cas system is not a plasmid-based system.

The bacteria in the population may, for example, be Gram-positive or Gram-negative bacteria. Preferably the bacteria are Gram-positive.

In some embodiments, the bacteria are spore-forming bacteria. In other embodiments, the bacteria are saccharolytic bacteria. The bacteria may be aerobic or anaerobic bacteria. Preferably, the bacteria are anaerobic bacteria. The bacteria may be thermophilic bacteria.

In yet other embodiments, the bacteria are able to convert a substrate into RCOOH, for example, into acetate and/or butyrate. In this context, R is an aliphatic C1-C5, preferably C1-3, alkyl or alkenyl group. The bacteria may also be able to convert the RCOOH into a solvent, preferably into one or more of acetone, ethanol and/or butanol.

In other embodiments, the bacteria are solvent-producing bacteria. As used herein, the term "solvent-producing" means that the bacteria are those which are capable of producing a solvent, preferably a solvent such as acetone, ethanol, propanol and/or butanol. In certain particularly preferred embodiments, the bacteria are capable of producing ethanol, acetone and butanol. Preferably, the bacteria are butanol-producing bacteria or butanol-tolerant bacteria.

In some preferred embodiments, the bacteria are of the genus *Clostridium*. Preferred *Clostridium* species include *C. acetobutylicum*, *C. arbusti*, *C. aurantibutyricum*, *C. beijerinckii*, *C. cellulovorans*, *C. cellulolyticum*, *C. thermocellum*, *C. thermobutyricum*, *C. pasteurianum*, *C. kluyveri*, *C. novyi*, *C. saccharobutylicum*, *C. thermosuccinogenes*, *C. thermopalmarium*, *C. saccharolyticum*, *C. saccharoperbutylacetonicum*, *C. tyrobutyricum*, *C. tetanomorphum*, *C. magnum*, *C. ljungdahlii*, *C. autoethanogenum*, *C. butyricum*, *C. puniceum*, *C. diolis*, *C. homopropionicum* and *C. roseum*.

In some preferred embodiments of the invention, the bacteria are *C. saccharoperbutylacetonicum* strain N1, e.g. N1-4. In other embodiments of the invention, the bacteria are *C. saccharoperbutylacetonicum* N1-4 (HMT). In yet other embodiments of the invention, the bacteria are *C. saccharoperbutylacetonicum* N1-504.

In other preferred embodiments, the bacteria are *C. pasteurianum* (e.g. DSM 525), *C. tyrobutyricum* (e.g. ATCC 52755), *C. saccharobutylicum* (e.g. NCP 258 and NCP 262) or *Clostridium* sp. DL-VIII.

In other preferred embodiments, the bacteria are from the genus *Bacillus*. In other preferred embodiments, the bacteria are from the order Actinomycetales.

In some embodiments of the invention, the bacteria are non-highly recombinogenic bacterium. As used herein, "non-highly recombinogenic" bacteria are bacteria where standard recombination techniques are inefficient to induce recombination, compared to recombination in "highly recombinogenic" strains. Various methods have been used to measure and to compare homologous recombination rates (HRR) between different species of bacteria. A useful table and discussion is provided in Vos and Didelot (2009) ("A comparison of homologous recombination rates in bacteria and archaea," The ISME Journal 3, 199-208; incorporated herein by reference). Vos and Didelot rank species according to recombination relative to point mutation (r/m) ratios; this can be interpreted as a general indication of HRR in a species. In particular, the r/m value is defined as the ratio of nucleotide changes as a result of recombination relative to point mutation. It may be estimated from the Multi Locus Sequence Typing (MLST) method of Maiden et al. (PNAS (USA) 95: 3140-3145 (1998); incorporated herein by reference) using the ClonalFrame computer package (Didelot and Falush (2007), Genetics 175: 1251-1266; incorporated herein by reference). Vos and Didelot (Table 1, which is specifically incorporated herein by reference) class strains from *Flavobacterium psychrophilum* to *Campylobacter jejuni* as having 'very high or high' homologous recombination rates (i.e. r/m values above 2). In a preferred embodiment of the current invention, the bacteria are not highly recombinogenic, i.e. the bacteria have intermediate, low or very low HRR, for example, the bacteria have r/m values below 2, more preferably below 1 as defined by Vos and Didelot.

In some embodiments, the bacteria are not modified to enhance recombinogenic activity. In particular, the recombinogenic activity of the bacteria is preferably not enhanced by the use of non-endogenous or exogenous recombination enzymes.

In other embodiments, the bacteria are preferably not *Streptococcus* or *E. coli*.

The IMR comprises a CRISPR PAM/Protospacer which is capable of being recognised by the bacteria's CRISPR/Cas system.

The PAM/Protospacer is the sequence in the bacterial genome that includes a functional combination of a PAM sequence and a Protospacer. This PAM/Protospacer sequence is one which is capable of being recognised by the CRISPR/Cas system that is being used and, upon production of the crRNA, it will be targeted by the chosen CRISPR/Cas system for degradation, leading to cell death of any bacteria which still comprise a functional CRISPR/PAM Protospacer.

As used herein, the term "functional CRISPR/PAM Protospacer" means a CRISPR PAM/Protospacer which is capable of being recognised by a crRNA which recognises the CRISPR/PAM Protospacer in the IMR. In some cases, a single mutation (e.g. in the PAM sequence) may be enough to render the CRISPR/PAM Protospacer non-functional.

PAM is an abbreviation for Protospacer-Adjacent Motif. PAM Elements are capable of being recognised by the bacterial CRISPR/Cas system. PAM Elements are generally 3-6 nucleotides long and are specific to each bacterial species.

The orientation of the PAM Element with respect to the Protospacer in the bacterial genome is important. In some bacterial species, the PAM Element is generally found at or near the 5' end of the Protospacer; in other species, the PAM Element is generally found at or near the 3' end of the Protospacer.

The PAM Element may be on either strand of the bacterial genome but the sequence chosen as the Cas Spacer Element should be on the same DNA strand as the PAM Element (so that the PAM Element and Protospacer are directly adjacent).

Some studies have found that almost any mutation in the PAM Element eliminates recognition by the CRISPR/Cas system (e.g. Jiang et al., Nature Biotech (March 2013), vol. 31, no. 3, pp. 233-239). The PAM/Protospacer Element must have a functional PAM Element, in addition to a functional Protospacer. As used herein, the term "functional PAM Element" or "CRISPR PAM Element which is functional in the bacteria" means that the PAM Element is capable of being recognised by the bacteria's endogenous CRISPR/Cas system or, if the bacteria do not have an endogenous CRISPR/Cas system, by the vector-based heterologous CRISPR/Cas system which has been introduced into the bacteria.

More than one sequence might be able to function as the PAM Element in the chosen bacterial species. For example, the I-E CRISPR-Cas system from *Escherichia coli* K-12 is known to have four functional PAM sequences (Gomaa et al. (2014). mBio, 5(1): e00928-13 DOI: 10.1128/mBio.00928-13), and in *C. saccharoperbutylacetonicum* N1-4 (HMT), at least four effective PAM sequences (CCC, CCT, CCA and CCG) have been identified using the method described in Example 2.

The ability of a PAM Element to function in a particular bacterial species may be tested by transforming the bacteria having a CRISPR/Cas system (either its endogenous CRISPR/Cas system or a heterologous plasmid-derived system) with a plasmid comprising a CRISPR Spacer, and an adjacent test-PAM Element. If the PAM Element is functional in the bacteria, the PAM Element-containing plasmid will be destroyed by the CRISPR/Cas system and the transformation efficiency will be significantly reduced. The concept is illustrated herein in Example 2.

The CRISPR Protospacer is the sequence within the bacterial genome which is targeted by the crRNA (provided that a compatible PAM Element is also appropriately located).

The IMR comprises a CRISPR PAM/Protospacer.

Preferably, the CRISPR PAM/Protospacer in the IMR falls within the region of DNA that corresponds to the Substitution Element in the Recombination Vector. In this embodiment, when the IMR is replaced by the Substitution Element in step (b), the CRISPR PAM/Protospacer is functionally removed from the bacterial genome. In some embodiments (e.g. where the mutation is a deletion), the region of DNA in the IMR that corresponds to the Substitution Element may have little or no degree of sequence identity with the Substitution Element. In such cases, the region of DNA that corresponds to the Substitution Element in the Recombination Vector will be the region of DNA in the IMR which is defined by the inner ends of the regions which correspond to the Homology Arms.

In other embodiments, the CRISPR PAM/Protospacer in the IMR falls within the region of DNA that corresponds to part of the Substitution Element and part of a 5'-Homology Arm in the Recombination Vector, or the CRISPR PAM/Protospacer in the IMR falls within the region of DNA that corresponds to a 5'-Homology Arm in the Recombination Vector. In these cases, a crossover event (between the Homology Arm and the corresponding sequence in the bacterial genome) which occurs 5' to the PAM/Protospacer in the IMR will result in the loss of the PAM/Protospacer from the bacterial genome. A crossover event which occurs in the PAM/Protospacer may render the PAM/Protospacer non-functional, i.e. incapable of being targeted by the crRNA. Hence bacteria which result from such crossovers will not be targeted by crRNA.

In other embodiments, the CRISPR PAM/Protospacer in the IMR falls within the region of DNA that corresponds to part of the Substitution Element and part of a 3'-Homology Arm in the Recombination Vector, or the CRISPR PAM/Protospacer in the IMR falls within the region of DNA that corresponds to a 3'-Homology Arm in the Recombination Vector. In these cases, a crossover event (between the Homology Arm and the corresponding sequence in the bacterial genome) which occurs 3' to the PAM/Protospacer in the IMR will result in the loss of the PAM/Protospacer from the bacterial genome. A crossover event which occurs in the PAM/Protospacer may render the PAM/Protospacer non-functional, i.e. incapable of being targeted by the crRNA. Hence bacteria which result from such crossovers will not be targeted by crRNA.

The person of skill in the art will appreciate that crossover events between the Homology Arms and the corresponding sequences in the bacterial genome are random events and that, if the PAM/Protospacer is in the region of DNA in the IMR which corresponds to the upstream Homology Arm for example, a crossover event resulting in replacement of the IMR with the Substitution Element may occur 3' to the PAM/Protospacer. In this case, the crRNA will still target the PAM/Protospacer resulting in the death of that bacterium. However, in other bacteria within the population, a crossover event resulting in replacement of the IMR with the Substitution Element may occur 5' to the PAM/Protospacer. In this case, the PAM/Protospacer will have been removed from the bacterial genome and hence the bacteria will not be targeted by the crRNA. It can be seen therefore that embodiments of the invention with PAM/Protospacers which fall within the regions of DNA corresponding to the Homology Arms are still capable of resulting in bacteria which comprise the Substitution Element and which either do not comprise the PAM/Protospacer or do not comprise a PAM/Protospacer which is capable of being recognised by the crRNA.

It is preferable for the PAM/Protospacer to be within the region of DNA that corresponds to the Substitution Element in the Recombination Vector or to be as close as possible to it in order to maximise the chance that the replacement of the IMR by the Substitution Element will also result in the removal of the PAM/Protospacer from the bacterial genome.

Preferably, therefore, the PAM/Protospacer in the IMR is present within a region of DNA which corresponds to:
(i) the Substitution Element;
(ii) the overlap between the upstream Homology Arm and the Substitution Element;
(iii) the overlap between the downstream Homology Arm and the Substitution Element;
(iv) the upstream Homology Arm in the Recombination Element; or
(v) the downstream Homology Arm in the Recombination Element.

More preferably, the PAM/Protospacer in the IMR is present within a region of DNA which corresponds to:
(i) the Substitution Element;
(ii) the overlap between the upstream Homology Arm and the Substitution Element; or
(iii) the overlap between the downstream Homology Arm and the Substitution Element.

Most preferably, the PAM/Protospacer in the IMR is present within a region of DNA which corresponds to the Substitution Element.

The aim of the step (a) of the process of the invention is transform the population of bacteria with the Recombination Vector. This can be achieved using standard recombination protocols and selected for using appropriate selection markers such as antibiotics.

The Recombination Vector comprises a Recombination Element, wherein the Recombination Element comprises a Substitution Element and Homology Arms.

The Substitution Element comprises the desired mutation.

The mutation may, for example, be a substitution, deletion or insertion of one or more nucleotides, or a combination of one or more substitution, deletion or insertion.

The Substitution Element may or may not be based on the sequence of the IMR which it is to replace. For example, the Substitution Element may have substantially the same DNA sequence as the IMR, but the Substitution Element may comprise a SNP, an insertion or a deletion compared to the DNA sequence of the IMR. In other cases, for example where it is desired to delete the IMR or to replace it with a different DNA, the Substitution Element may not have any significant degree of sequence identity with the IMR.

In some embodiments, the mutation is or comprises a single nucleotide polymorphism (SNP) compared to the sequence of the IMR. In such embodiments, the mutation is preferably in the PAM/Protospacer, so that the PAM/Protospacer becomes no longer functional (i.e. no longer recognised by the CRISPR/Cas system). If not, then the mutation may be in another part of the sequence of the Substitution Element.

In other embodiments, the mutation may comprise one or more deletions of one or more nucleotides compared to the sequence of the IMR. The deletion(s) may be in-frame or not in-frame. Preferably, the deletion includes at least part of the PAM or PAM/Protospacer so that the PAM/Protospacer becomes no longer functional (i.e. no longer recognised by the CRISPR/Cas system).

In yet other embodiments, the mutation comprises one or more insertions of one or more nucleotides compared to the sequence of the IMR. In some embodiments, the insertion is within the PAM/Protospacer such that the PAM/Protospacer becomes no longer functional (i.e. no longer recognised by the CRISPR/Cas system). The insertion may in an in-frame insertion or an out-of-frame insertion.

In other embodiments, the mutation is an insertion which replaces all or part of the PAM/Protospacer. Preferably, the PAM or PAM/Protospacer is deleted, or mutated so that it is no longer functional (i.e. no longer recognised by the CRISPR/Cas system).

In the event that the desired mutation (e.g. a SNP, insertion or deletion) does not affect the PAM/Protospacer, then an additional mutation must be made in the PAM/Protospacer Element to render it non-functional in the bacterial species of interest. For example, a silent mutation may be made in the PAM/Protospacer Element (if the PAM/Protospacer sequence is a coding sequence).

In embodiments where the desired mutation is not in the actual PAM/Protospacer, it is preferable to keep the distance between the PAM Element and the site of the mutation to a minimum. The further apart the PAM Element and the site of the mutation are, the more the chance of a recombination event happening in the space between them. This may result in a bacteria carrying a mutated PAM Element but being wild-type for the desired mutation. The mutated PAM could be up to 1500 bp from the desired mutation. The distance between the PAM site and the desired mutation is preferably 100 bp or less. More preferably the distance between the PAM Element and the site of the desired mutation is less than 50 nucleotides, even more preferably less than 25 nucleotides and most preferably less than 10 nucleotides.

The length of the Substitution Element may be from 1-100,000 nucleotides, preferably 1-50,000 or 1-10,000 nucleotides, more preferably from 1-5000, 1-2500, 1-1000, 1-500, 1-50 or 1-10 nucleotides.

The minimum size of the Substitution Element is defined by the desired mutation. Hence in cases where the mutation is or comprises a SNP, the Substitution Element may comprise a single nucleotide. In cases where the mutation is a deletion which includes the PAM Element, the Substitution Element may be 0 nucleotides. For an insertion, the Substitution Element is the length of the DNA to be inserted.

In some embodiments of the invention, the Substitution Element does not comprise a selectable marker which confers a selectable phenotype on host bacterial cells into whose genomes the Substitution Element has been inserted.

In other embodiments of the invention, the Substitution Element does not comprise a first element of a selectable marker which is capable of being juxtaposed with a second element of the selectable marker in the genome of the bacteria in order to produce a selectable marker allele which confers a selectable phenotype on host bacterial cells into whose genomes the Substitution Element has been inserted.

The Recombination Element also comprises:
(ii) Homology Arms which flank the Substitution Element, wherein the Homology Arms are capable of promoting the replacement of all or part of the IMR in the bacterial genome with an element which comprises the Substitution Element.

The Homology Arms promote homologous recombination (double cross-over) between the Recombination Element and the bacterial genome which results in the replacement of the IMR with an element which comprises the Substitution Element.

Preferably, there are two Homology Arms, one of which is 5' to the Substitution Element and one of which is 3' to the Substitution Element.

The upstream (5') Homology Arm comprises a stretch of DNA whose sequence has identity to a stretch of DNA that lies in the 5' end of the IMR.

The downstream (3') Homology Arm comprises a stretch of DNA whose sequence has identity to a stretch of DNA that lies in the 3' end of the IMR.

Preferably, the degree of sequence identity between the 5' Homology Arm and the corresponding sequence in the bacterial genome is at least 80%, more preferably at least 90%, 95% or 99% or it is 100%. Preferably, the degree of sequence identity between the 3' Homology Arm and the corresponding sequence in the bacterial genome is at least 80%, more preferably at least 90%, 95% or 99% or it is 100%.

The Homology Arms may each independently be 50-1500 or 200-1000 nucleotides in length, preferably 500-1000 and more preferably independently 700-900 nucleotides in length. Most preferably, the Homology Arms are each independently about 800 nucleotides in length.

As used herein, the term "an element which comprises the Substitution Element" generally refers to an element which comprises part of the upstream Homology Arm, the Substitution Element and part of the downstream Homology Arm. Such an element will replace part or all of the IMR once double cross-over has been carried out.

All or part of the IMR in the bacterial genome will be replaced with an element which comprises the Substitution Element. The precise amount of IMR which is replaced will be dependent upon the location of the cross-over events between the Homology Arms in the Recombination Vector and the corresponding regions in the IMR.

The Recombination Vector is preferably a circular vector.

The Recombination Vector preferably has an Origin Element, most preferably a Gram positive Origin Element (for example "pBP1"). In some preferred embodiments the Recombination Vector Origin Element is compatible with the Killing Vector Origin Element.

The Recombination Vector may also comprise an appropriate selection marker (e.g. antibiotic resistance gene). Preferably, the Recombination Vector and the Killing Vector have different selection markers.

The Recombination Element does not comprise a CRISPR PAM/Protospacer which is capable of being recognised by a crRNA which recognises the CRISPR/PAM Protospacer in the IMR. This is to ensure that a new CRISPR PAM/Protospacer which is capable of being recognised by a crRNA is not inserted into the bacterial genome following a double cross-over event.

Step (b) comprises culturing the population of bacteria under conditions wherein, in one or more bacteria within the population, all or part of the IMR in the genomes of those bacteria is replaced by an element which comprises the Substitution Element and whereby the CRISPR PAM/Protospacer is removed from the IMR in the genomes of those bacteria or is rendered incapable of being recognised by a crRNA which recognises the CRISPR/PAM Protospacer in the IMR.

In many bacterial species, this replacement step is not very efficient. Hence it is generally not expected that this step will be successful in all of the bacteria within the population.

In this step, the bacteria which have been transformed with the Recombination Vector are cultured to encourage a double crossover event wherein an element comprising the Substitution Element becomes integrated into the bacterial genome and the IMR loops out on the Vector.

In the methods of this invention, use is not made of recombineering techniques. In particular, the Substitution Element is not placed on a linear DNA.

Double cross-over events are desired wherein the CRISPR PAM/Protospacer is removed from the IMR in the genomes of those bacteria or is rendered incapable of being recognised by a crRNA which recognises the CRISPR/PAM Protospacer in the IMR.

Preferably, one or more transformed bacteria are isolated and sub-cultured further on selective media (e.g. with antibiotics) to maintain the Recombination Vector (one or more times, e.g. 1-5 times) to produce one or more further populations of bacteria, some of which will undergo the desired double crossover event.

Suitable conditions for culturing the bacteria will be readily known in the art. Such conditions are, for example, described in "Clostridia Biotechnology and Medical Applications", Eds H. Bahl and P. Durre, ISBN 3-527-30175-5, especially section 3.4 "Growth conditions and nutritional requirements". Details are also given in Bergey's Manual of Systematic Bacteriology, Volume appropriate to the chosen phylum of bacteria, e.g. Volume Three for the Firmicutes, ISBN 978-0-387-95041-9.

In step (c) of the process of the invention, the population of bacteria is transformed with a Killing Vector which is capable of producing a crRNA which targets the CRISPR PAM/Protospacer in the IMR of any bacteria in the population from which the CRISPR PAM/Protospacer has not been removed or rendered incapable of being recognised by the crRNA, thereby promoting the CAS endonuclease-induced cleavage of those CRISPR PAM/Protospacers which are recognised by the crRNA and the subsequent death of those bacteria.

The aim of the third step of the method of the invention is to select against bacterial cells within the population of bacteria whose genomes still comprise the functional PAM/Protospacer. The crRNA will target any bacterial cells in which only a single crossover event has occurred; it will also target any cells which have no crossover events or which have reverted to wild-type through double crossover. Because these will all have a wild-type (i.e. functional) PAM/Protospacer, these bacteria will be killed.

Consequently, essentially the only bacterial cells which should be alive after this step should be bacterial cells which have the Substitution Element which comprises the desired mutation.

The bacteria which have been transformed with the Killing Vector are preferably cultured at this time in the presence of a selectable marker (e.g. antibiotic resistance) which is specific for the Killing Vector only (and not the Recombination Vector).

The term "crRNA" means CRISPR RNA. crRNAs are short single-stranded RNA molecules consisting of short Direct Repeat sequences flanking a target Spacer sequence to be cleaved by the CRISPR/Cas system.

In preferred embodiments, the Killing Vector comprises:
(i) a Cas Leader Element
(ii) a first Cas Direct Repeat Element
(iii) a Cas Spacer Element, and
(iv) a second Cas Direct Repeat Element.

The "Cas Leader Element" is a DNA element which is generally found upstream of the first repeat in the Direct Repeat cluster. It helps to promote the production of crRNA, i.e. it functions as a RNA promoter. Numerous Cas Leader sequences have been identified to date and their sequences may readily be established in any particular Cas system. Preferably, the Cas Leader sequence is one which corresponds to the CRISPR/Cas system which is present in the bacterial population which is being transformed.

The Cas Direct Repeat sequences are DNA elements which are recognised by the CRISPR/Cas system which is present in the population of bacteria. These Direct Repeats are generally 25-35 nucleotides in length, more generally about 29 or 30 nucleotides in length.

The Direct Repeats do not need to be of identical sequence (generally a difference of 1-2 nucleotides is tolerated by the Cas protein). The Direct Repeats generally have palindromic regions which are capable of forming hair-pin loops.

The DNA sequence of Direct Repeats which are suitable for any one CRISPR/Cas system may readily be found from any inspection of the CRISPR/Cas direct repeat-Spacer cluster of that system.

The Cas Spacer Element comprises a sequence of 20-50 nucleotides (preferably 30-40, more preferably 36-38 nucleotides) with a high level of sequence identify to the 20-50 nucleotides (preferably 30-40, more preferably 36-38 nucleotides) which are found (preferably immediately) 5' to the PAM Element in the PAM/Protospacer or (preferably immediately) 3' to the PAM Element in the PAM/Protospacer, depending on the preference of the CRISPR/Cas system which is present in the bacterial population of interest.

Preferably, the PAM Element in the IMR (in the bacterial genome) is directly adjacent to the start of the Protospacer sequence (in the bacterial genome).

The degree of sequence identity between the Protospacer (in the genomic DNA) and the Spacer Element sequence (e.g. in the Killing Vector) is preferably at least 80%, more preferably at least 85%, 90%, 95%, 96%, 97%, 98% or 99%, or is 100%.

Preferably, the Cas Spacer sequence is selected such that there is a low probability of interaction with a non-Protospacer Element.

It is possible to use the process of the invention to target more than one Protospacer in the bacterial genome at a time. In this case, the Killing Vector comprises more than one Cas Spacer Element, wherein each Cas Spacer Element is flanked by Direct Repeats.

Unlike the Protospacer Element in the bacterial genome, the Spacer Element must not have an associated PAM Element.

The Killing Vector has an Origin (preferably a Gram positive Origin, e.g. pCB102) which is compatible with the Origin of the Recombination Vector.

Preferably, the Origins for the Recombination Vector and the Killing Vector are different.

The Recombination Vector and the Killing Vector may comprise antibiotic-resistance elements or other selection markers, thus allowing the Vectors to be selected for independently, e.g. in the presence of certain antibiotics, for example chloramphenicol, erythromycin, tetracycline, spectinomycin, streptomycin etc. Preferably, the Recombination Vector and the Killing Vector comprise antibiotic-resistance elements which allow for their independent selection on different antibiotics.

Once the Killing Vector has been transformed into the bacterial population, the Cas Leader sequence will promote the transcription of the crRNA which will comprise the Direct Repeats and the Cas Spacer Element. The crRNA will then target any PAM/Protospacers in the bacterial genome which have not been eliminated by replacement of the IMR with an element which comprises the Substitution Element. Such PAM/Protospacers will then be cleaved by the CRISPR/Cas system, resulting in the death of those bacteria which still have such PAM/Protospacers in their genomes.

Percentage amino acid sequence identities and nucleotide sequence identities may be obtained using the BLAST methods of alignment (Altschul et al. (1997), "Gapped BLAST and PSI-BLAST: a new generation of protein database search programs", Nucleic Acids Res. 25:3389-3402; and www.ncbi.nlm.nih.gov). Preferably the standard or default alignment parameters are used.

Standard protein-protein BLAST (blastp) may be used for finding similar sequences in protein databases. Like other BLAST programs, blastp is designed to find local regions of similarity. When sequence similarity spans the whole sequence, blastp will also report a global alignment, which is the preferred result for protein identification purposes. Preferably the standard or default alignment parameters are used. In some instances, the "low complexity filter" may be taken off.

BLAST protein searches may also be performed with the BLASTX program, score=50, wordlength=3. To obtain gapped alignments for comparison purposes, Gapped BLAST (in BLAST 2.0) can be utilized as described in Altschul et al. (1997) Nucleic Acids Res. 25: 3389. Alternatively, PSI-BLAST (in BLAST 2.0) can be used to perform an iterated search that detects distant relationships between molecules. (See Altschul et al. (1997) supra). When utilizing BLAST, Gapped BLAST, PSI-BLAST, the default parameters of the respective programs may be used.

With regard to nucleotide sequence comparisons, MEGABLAST, discontiguous-megablast, and blastn may be used to accomplish this goal. Preferably the standard or default alignment parameters are used. MEGABLAST is specifically designed to efficiently find long alignments between very similar sequences. Discontiguous MEGABLAST may be used to find nucleotide sequences which are similar, but not identical, to the nucleic acids of the invention.

The BLAST nucleotide algorithm finds similar sequences by breaking the query into short subsequences called words. The program identifies the exact matches to the query words first (word hits). The BLAST program then extends these word hits in multiple steps to generate the final gapped alignments. In some embodiments, the BLAST nucleotide searches can be performed with the BLASTN program, score=100, wordlength=12.

One of the important parameters governing the sensitivity of BLAST searches is the word size. The most important reason that blastn is more sensitive than MEGABLAST is that it uses a shorter default word size (11). Because of this, blastn is better than MEGABLAST at finding alignments to related nucleotide sequences from other organisms. The word size is adjustable in blastn and can be reduced from the default value to a minimum of 7 to increase search sensitivity.

A more sensitive search can be achieved by using the newly-introduced discontiguous megablast page (www.ncbi.nlm.nih.gov/Web/Newsltr/FallWinter02/blast-lab.html). This page uses an algorithm which is similar to that reported by Ma et al. (Bioinformatics. 2002 March; 18(3): 440-5). Rather than requiring exact word matches as seeds for alignment extension, discontiguous megablast uses non-contiguous word within a longer window of template. In coding mode, the third base wobbling is taken into consideration by focusing on finding matches at the first and second codon positions while ignoring the mismatches in the third position. Searching in discontiguous MEGABLAST using the same word size is more sensitive and efficient than standard blastn using the same word size. Parameters unique for discontiguous megablast are: word size: 11 or 12; template: 16, 18, or 21; template type: coding (0), non-coding (1), or both (2).

As used herein, the term "transformation" and "transforming" refers to any step by which the Recombination Vector or the Killing Vector are inserted into the bacterial cells. Hence it includes any form of electroporation, conjugation or transfection, inter alia.

Step (d) comprises selecting or isolating one or more bacteria whose genomes comprise the Substitution Element comprising the desired mutation.

Bacteria carrying the desired mutation(s) will easily lose the WT (wild type) IMR due to the fact that it will be looped out on the Recombination Vector. Such modified Recombination Vectors may then be easily lost from the bacterial population because the Killing Vector will recognise the PAM/Protospacer now on the vector. Therefore from this point on the selection marker (e.g. antibiotic) used to originally select for the Recombination Vector should be withdrawn.

Bacteria that have lost the Killing Vector may readily be isolated using media which do not contain the Killing Vector selection marker (e.g. antibiotic). Alternative methods may also be used. In addition, cells may be subjected to certain stresses that might increase the rate of plasmid loss from the cell, for example heat shock or electroporation.

The bacteria which are selected for or isolated will be live bacteria.

The invention further provides a process for making mutated bacteria, which comprises mutating bacteria by a process of the invention.

The invention also provides bacteria whose genome has been mutated by a process of the invention.

BRIEF DESCRIPTION OF THE FIGURES

FIG. 2 shows an alignment of Direct Repeat sequences from a number of clostridial species.

FIG. 5 shows Sanger sequencing data from two colonies carrying the SNPs that were created using the described technology.

EXAMPLES

Example 1: Alignment of Direct Repeat Sequences from a Number of Clostridial Species Aim: To identify some Direct Repeat sequences that could be used in the process of the invention.
Method:
Direct Repeats and the Spacer sequences were found using the CRISPRFinder program Grissa, I., Vergnaud, G., & Pourcel, C. (2007). CRISPRFinder: a web tool to identify clustered regularly interspaced short palindromic repeats. Nucleic Acids Res., 35, W52-7.

Results:
A selection of Direct Repeat sequences from a number of clostridial species are displayed in FIG. 2. In some cases the specific strain has more than one sequence so the most frequently used Direct Repeat sequence(s) is included here. Abbreviations are as follows: C_saccharoper=*Clostridium saccharoperbutylacetonicum* N1-4 (HMT) or N1-504), C_saccharob=*Clostridium saccharobutylicum* (NCP258 or NCP262, _1 and _2 refer to the 2 main DR clusters), C_tyro=*Clostridium tyrobutyricum* (ATCC 52755, _1 and _2 refer to the 2 main DR clusters), C_pasteurianum=*Clostridium pasteurianum* (DSM 525), C_autoethanogenum=*Clostridium autoethanogenum* (DSM10061), C_sp_DLVIII=*Clostridium* sp. (DL-VIII).

Example 2: Confirming the PAM Sequence in *C. saccharoperbutylacetonicum* N1-4 (HMT)

Aim: To demonstrate how to test effectiveness of putative PAM sequences.
Method:
The sequence of Spacer_53 from the main Direct Repeat cluster of *C. saccharoperbutylacetonicum* N1-4 (HMT) was cloned into the clostridial shuttle vector, pMTL83251. Immediately adjacent to the 5' end of this Spacer Element various different trinucleotide combinations were incorporated, including the predicted PAM sequences CCC, CCG, OCT and a non-PAM sequence GAC. When correctly combined with a functional PAM sequence, the Spacer Element functions as a Protospacer.

The plasmids were transformed into *C. saccharoperbutylacetonicum* N1-4 (HMT) using standard electroporation protocols followed by an overnight recovery stage in Clostridial Growth Medium (CGM) also containing 5% glucose. The mixture was then spread onto CGM agar plates containing 5% glucose and 40 µg/ml erythromycin and left for at least 48 hours in an anaerobic cabinet at 32° C. Colonies were then counted to determine the change in transformation efficiency compared with transformation of the empty vector.

CGM medium was prepared by dissolving the following amounts in 750 ml dH$_2$O: 5.0 g yeast extract, 0.75 g K$_2$HPO$_4$, 0.75 g KH$_2$PO$_4$, 0.40 g MgSO$_4$.7H$_2$O, 0.01 g FeSO$_4$.7H$_2$O, 0.01 g MnSO$_4$.4H$_2$O, 1.0 g NaCl, 2.0 g (NH$_4$)$_2$SO$_4$, 2.0 g asparagine (and 15 g bacteriological agar no.1 if making solid medium) and autoclaved. The pH of the medium was not adjusted (usually in the region of 6.6). A glucose solution (50 g glucose dissolved in 250 ml dH$_2$O to give a 20% (w/v) solution) was prepared and autoclaved separately. Once cool, the glucose and CGM solutions were combined as needed.

Figure 1:
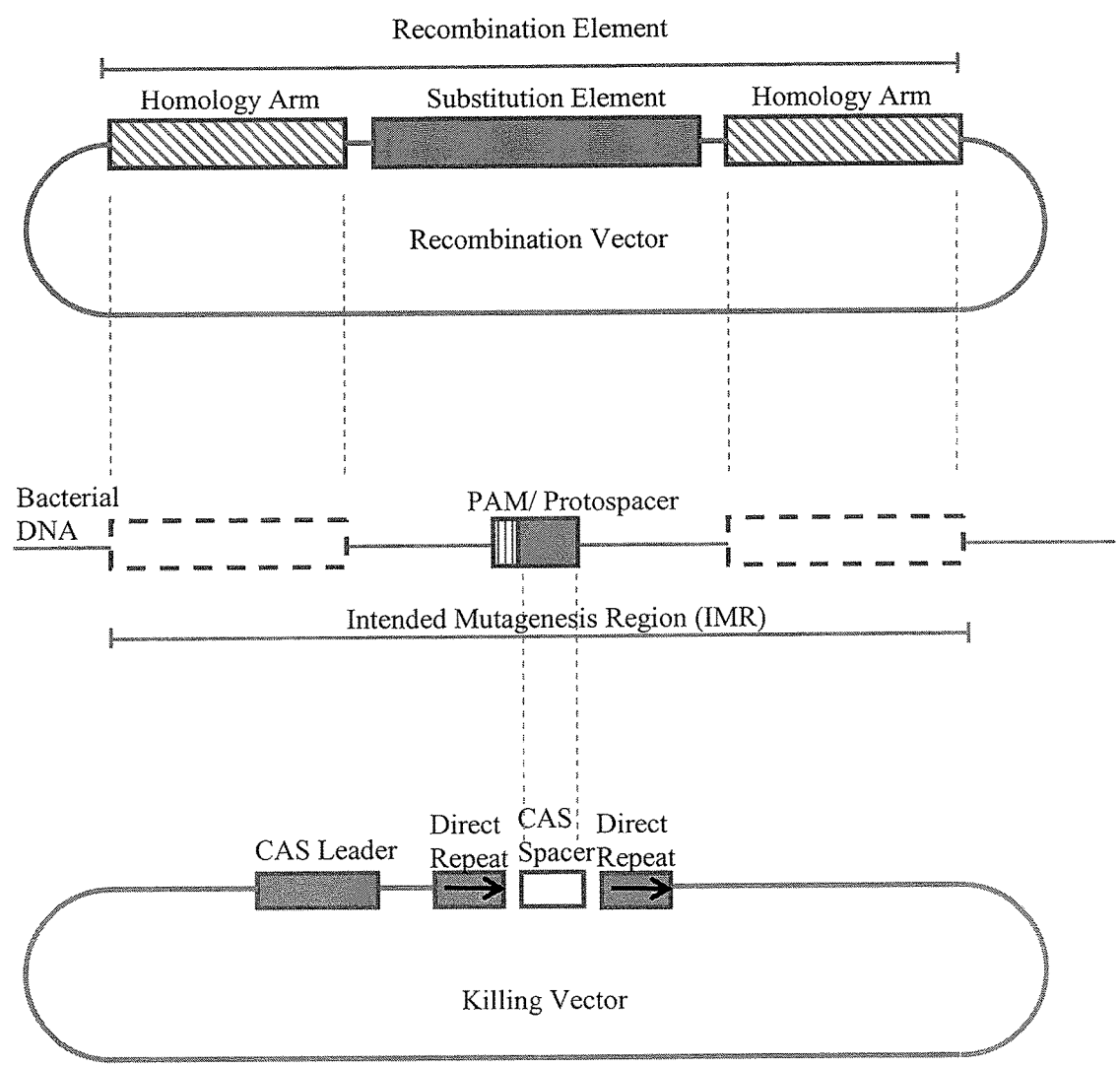
FIG. 1 illustrates the relationship between the elements of the Recombination Vector, the endogenous bacterial DNA and the Killing Vector in one embodiment of the invention.
Figure 3:
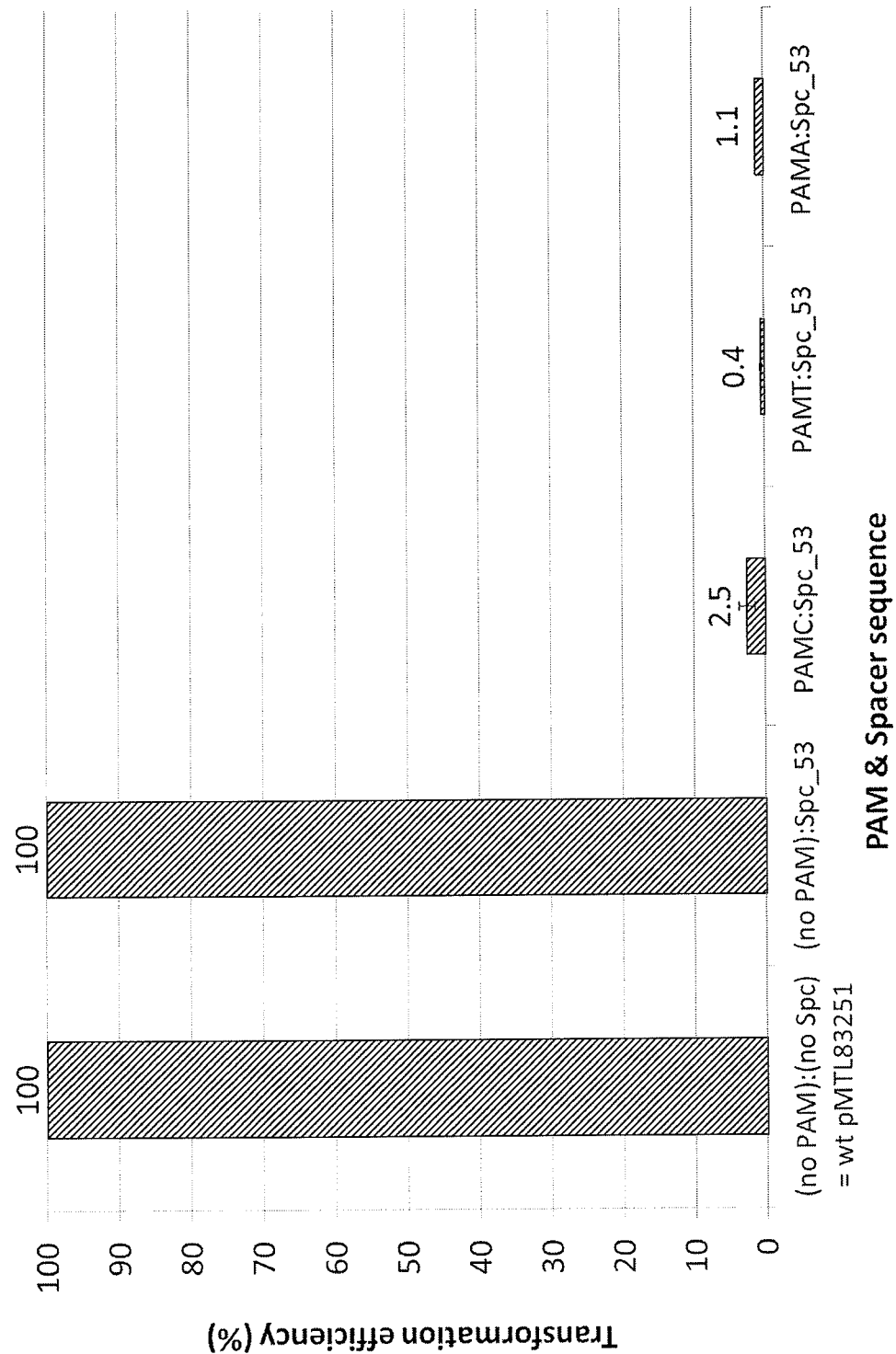
FIG. 3 shows the effect of the PAM sequence on the transformation efficiency of plasmids into *C. saccharoperbutylacetonicum* N1-4 (HMT).

Results:
The relative efficiencies of transformation of the different plasmids are presented in FIG. 3. Both the empty plasmid pMTL83251 and the plasmid carrying Spacer_53 without a PAM sequence gave a lawn of colonies. Plasmids carrying Spacer_53 adjacent to a 5' CCC (PAMC), CCT (PAMT) or CCA (PAMA) yielded significantly fewer colonies.

Example 3: Making a SNP Replacement in *C. saccharoperbutylacetonicum* N1-4 (HMT)

Aim: To show how specific point mutations can be made using the disclosed technique.
Method:
An IMR sequence was chosen for mutation in the genomic DNA of *C. saccharoperbutylacetonicum* N1-4

(HMT). From the sequence, a candidate Protospacer Element was identified adjacent to a PAM (in this example CCA). The sequence of this PAM/Protospacer Element is given in Table 1. A Recombination Vector was designed comprising a Substitution Element flanked by a pair of Homology Arms, each arm being approximately 800 bp long. The Substitution Element (Table 1) carries three SNPs relative to the original genomic sequence of the PAM/Protospacer Element. One of the three SNPs was incorporated to mutate the PAM sequence to CTA; the other two were designed to remove a restriction site (uppercase and underlined).

The Recombination Vector was based on the clostridial shuttle vector pMTL82154. It was transformed into *C. saccharoperbutylacetonicum* N1-4 (HMT) using standard electroporation protocols. Successful transformants were selected for based on resistance to chloramphenicol (50 µg/ml). Single colonies were picked and transferred into liquid Reinforced Clostridial Medium (RCM) containing chloramphenicol. They were subcultured four or more times in order to promote the double crossover event and loop out of the WT sequence.

RCM semi-solid medium was prepared as follows: 3 g·L$^{-1}$ yeast extract, 10 g·L$^{-1}$ Lab-Lemco powder, 10 g·L$^{-1}$ peptone, 5 g·L$^{-1}$ glucose, 1 g·L$^{-1}$ soluble starch, 5 g·L$^{-1}$ sodium chloride, 3 g·L$^{-1}$ sodium acetate, 0.5 g·L$^{-1}$ cysteine hydrochloride, 0.5 g·L$^{-1}$ agar, pH adjusted to 6.8±0.2, then sterilised by autoclaving at 121° C.

These cultures were then transformed with a Killing Vector comprising the Leader sequence and a Spacer Element corresponding to the candidate Protospacer identified above, the Spacer Element being flanked by direct repeat sequences on a pMTL83251 plasmid backbone. Cells were allowed to recover overnight in CGM with 5% glucose before being plated onto CGM-agar containing 5% glucose plus 40 µg/ml erythromycin.

The Spacer Element (Table 1) present on the Killing Vector effectively turns the corresponding sequence in the genome into a functional Protospacer Element. This Spacer carried by the Killing Vector targets the WT sequence only and the bacterium's own Cas system perceives its own genomic DNA as invading DNA and cleaves it resulting in cell death. The only cells that recover after transformation with the Killing Vector must therefore have recombined the Substitution Element into their genomic DNA.

TABLE 1

Sequences of the PAM/Protospacer Element, the Spacer Element and the Substitution Element used in Example 3

PAM/Protospacer Element sequence:
CCActtgctgctccagcgtttcctaggggaccatatagattcatatagat
tt (SEQ ID NO: 1)

Spacer Element sequence in Killing Vector:
cttgctgctccagcgtttcctaggggaccatatagat
(SEQ ID NO: 2)

Partial sequence of Recombination Vector showing Substitution Element sequence (boxed):

c TActtgctgctccagcgtttccAagA ggaccatatagattcatatagat tt (SEQ ID NO: 3)

High Resolution Melt Curve Analysis (HRM)

Colonies selected by the above process were screened using high resolution melt curve analysis to identify the presence of SNPs compared to WT sequence. A 1.1 kb region containing the intended location of the SNPs was amplified using primers that would only amplify products from the bacterial chromosome. A second PCR was then carried out on this product to amplify a shorter fragment (85 bp) covering the intended SNP region using Precision Melt supermix (BioRad). After the PCR, a melt curve was run from 70° C. to 80° C. with 0.2° C. increments to give a melt curve for each of the colonies tested.

The 1.1 kb PCR products from the genomic DNA specific PCRs were also screened for the target mutations by restriction enzyme digest (as two of the SNPs destroyed an AvrII site) and then by DNA sequencing.

Results:

Two promising colonies were obtained after transformation with the Killing Vector, named A and B. This method therefore significantly reduces the number of colonies that need to be screened to identify the required mutations.

Figure 4:
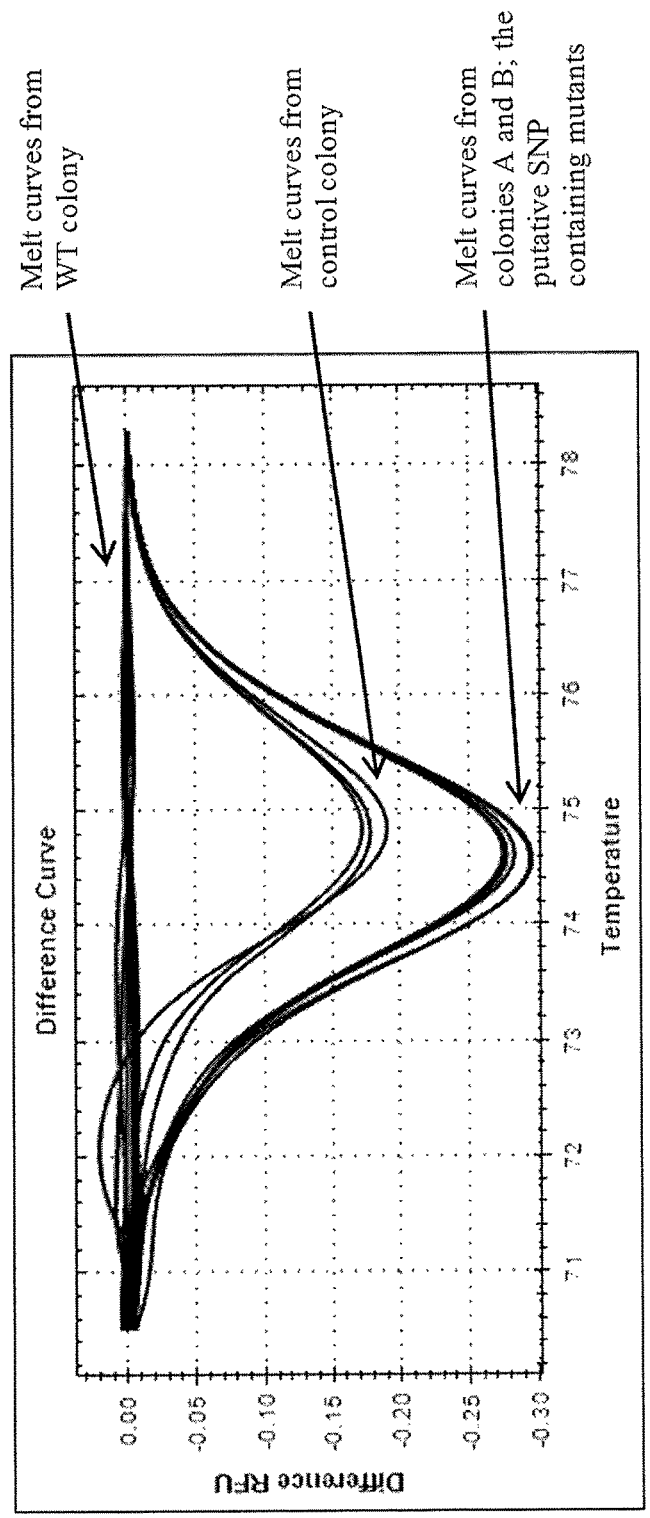
FIG. 4 shows High Resolution Melt curve analysis of mutated and WT DNA sequences for the SNP replacement example.

Colonies A and B were analysed by HRM and compared to both the WT and a control strain (carrying one of the three mutations being incorporated), as shown in FIG. 4. The difference in the melt curves for colonies A and B compared to those for WT or control indicated that the region of the genome across the SNP sequence had been changed compared to the WT strain.

Sanger Sequencing

Sequencing results for the 1.1 kb PCR products from the genomic specific PCRs generated for the above HRM analysis are shown in FIG. 5. The alignment of "WT"=Sequence obtained from WT cultures, "Expected mutations"=in silico prediction of expected mutations, "Control sequence"=Sequence obtained from a mutant strain carrying the PAM mutation only, "Col A" and "Col B"=strains made as described, using the *C. saccharoperbutylacetonicum* N1-4 (HMT) Cas system, was created using Seqman Pro (DNAStar, Lasergene).

It confirms that the changes in the HRM curves were due to the three SNPs which had been introduced.

Subsequent sequencing over this entire region showed no additional mutations had been introduced (data not shown).

Example 4: Making a Precise Deletion in *C. saccharoperbutylacetonicum* N1-4 (HMT)

Aim: To show how the process of the invention can be used to make precise deletions within the genome.

Method:

An N-terminal deletion mutant was designed in which 12 amino acids were removed from the start of a selected gene and a new start codon added, resulting in an in-frame truncation of the sequence in *C. saccharoperbutylacetonicum* N1-4 (HMT), named "ΔNt". Two additional SNPs were also incorporated to remove an AwII restriction site. Within this WT region a candidate Protospacer Element was identified adjacent to a PAM (in this example CCA). The sequence of this region with the PAM/Protospacer Element and the region for deletion highlighted is given in Table 2. A Recombination Vector was designed comprising a Substitution Element flanked by a pair of Homology Arms, each arm being approximately 800 bp long. The Substitution Element (Table 2) carries the 36 base pair deletion and new start codon relative to the original genomic sequence.

The Recombination Vector was based on the clostridial shuttle vector pMTL82154. It was transformed into *C.* saccharoperbutylacetonicum N1-4 (HMT) using standard electroporation protocols and was selected for based on resistance to chloramphenicol (50 µg/ml). Single colonies were picked and transferred into liquid Reinforced Clostridial Medium (RCM) containing chloramphenicol. They were subcultured three or more times to promote the double crossover event to loop out the WT sequence.

These cultures were then transformed with a Killing Vector comprising the Leader sequence and a Spacer Element corresponding to the candidate Protospacer identified above, the Spacer Element being flanked by direct repeat sequences on a pMTL83251 plasmid backbone. Cells were allowed to recover overnight in CGM with 5% glucose before being plated onto CGM-agar containing 5% glucose plus 40 µg/ml erythromycin.

The only cells that recover after transformation with the Killing Vector must therefore have recombined the Substitution Element into their genomic DNA resulting in precise deletion of the targeted 12 amino acids at the N-terminus of the gene.

TABLE 2

Sequences of the PAM/Protospacer Element, the Spacer Element and the Substitution Element used in Example 4

WT DNA sequence in the genomic DNA showing the region for deletion(i.e. to be replaced with the Substitution Element), boxed, and the PAM/Protospacer in italics:

aggttgattattttt[atgttagaaagtgaagtatctaaacaaattacaact]

[CCActtgctgctccagcgtttcctagg]ggaccatatagatttcataatag agaatatctaaacattattt (SEQ ID NO: 4)

Spacer sequence in Killing Vector:
cttgctgctccagcgtttcctaggggaccatatagat
(SEQ ID NO: 2)

Partial sequence of Recombination Vector showing Substitution Element sequence (boxed):
aggttgattattttt[ATGcttgctgctccagcgtttccAagA]ggaccatat agatttcataatagagaatatctaaacattattt (SEQ ID NO: 5)

Figure 6:
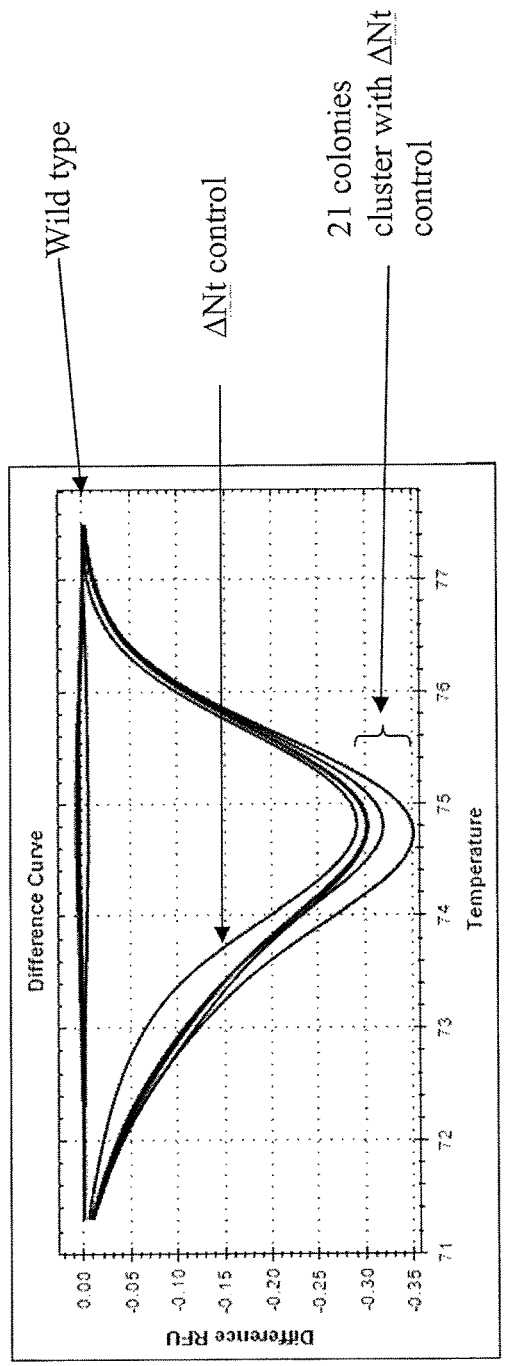
FIG. 6 shows High Resolution Melt curve analysis of mutated and WT DNA sequences for the targeted deletion example.
Figure 7:
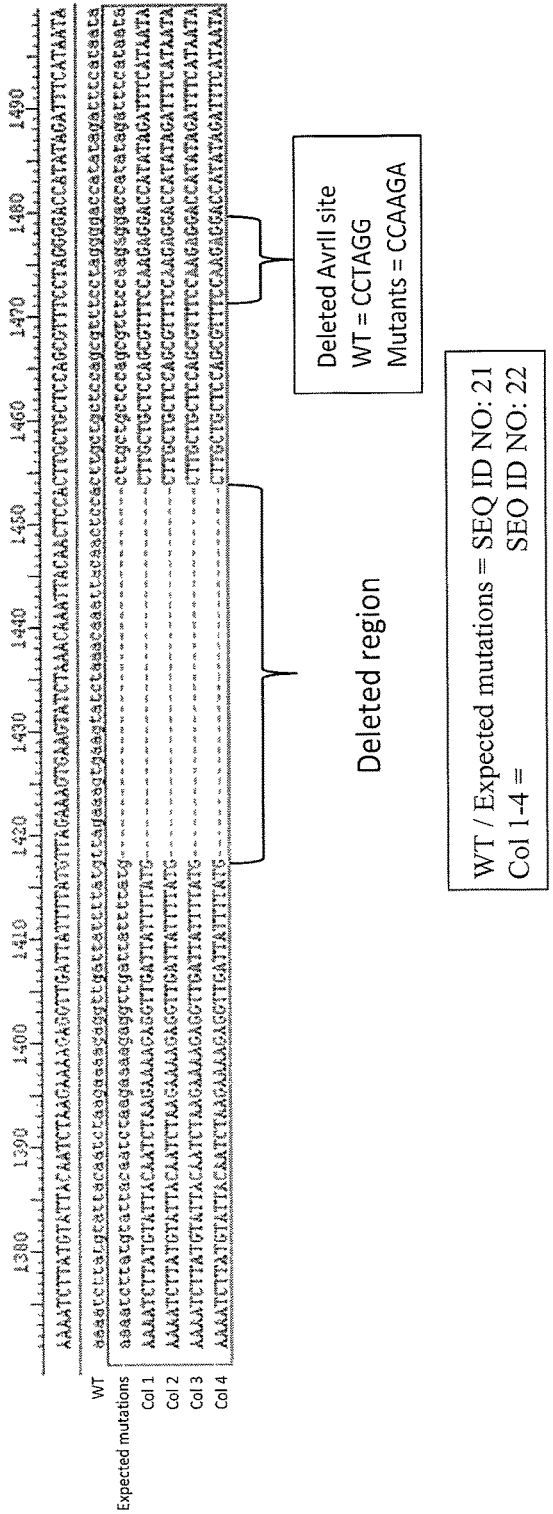
FIG. 7 shows the Sanger sequencing result for the targeted deletion example.

Results:

Approximately 30 promising colonies were screened after transformation with the Killing Vector and of these 21 showed a different HRM curve to the WT control (FIG. 6). Further analysis and Sanger sequencing of a few of these 21 colonies indicated they all carried the intended N-terminal deletion (FIG. 7).

Example 5: Integration of New DNA into the *C. saccharoperbutylacetonicum* N1-4 (HMT) Genome Aim: To detail how to use the process of the invention to integrate new DNA into genomic DNA.

Method:

A Recombination Vector was designed based on the pMTL82154 backbone. It carries approx. 800 bp up and downstream from a region in the *C. saccharoperbutylacetonicum* N1-4 (HMT) genome chosen for its absence of coding sequence. A promoter based on the thiolase promoter sequence has been cloned between the two Homology Arms and genes for insertion will be cloned downstream of this promoter, as the Substitution Element, for expression in *C. saccharoperbutylacetonicum* N1-4 (HMT). At the 5' end of the 3' Homology Arm, the PAM/Protospacer Element sequence (in the IMR) that will be recognised in the WT cell by the Killing Vector carries a single SNP in the PAM sequence. This will ensure that only cells carrying the integrated DNA will survive when the Killing Vector is transformed into the cells.

The Killing Vector has been constructed based on pMTL83251. It carries the leader sequence and two Direct Repeats flanking a Spacer Element designed from within the intergenic region chosen as the integration site. The Killing Vector has been tested in *C. saccharoperbutylacetonicum* N1-4 (HMT) and has been shown to kill WT cells. (Transformation of this vector into *C. saccharoperbutylacetonicum* N1-4 (HMT) resulted in no colonies being recovered.)

The integration vector has been transformed into *C. saccharoperbutylacetonicum* N1-4 (HMT) using electroporation and transformants were selected for based on chloramphenicol resistance. After subculturing 3 or more times, the Killing Vector will then be introduced to remove any WT cells from the population, leaving only those cells that have integrated the new DNA into their genomes.

SEQUENCE LISTING FREE TEXT

SEQ ID NO: 3 <223> Partial sequence of Recombination Vector with Substitution Element SEQ ID NO: 5 <223> Partial sequence of Recombination Vector with Substitution Element SEQ ID NO: 18 <223>*Clostridium saccharoperbutylacetonicum* sequence with mutated PAM site SEQ ID NO: 19 <223> Mutated *Clostridium saccharoperbutylacetonicum* sequence SEQ ID NO: 20 <223> Mutated *Clostridium saccharoperbutylacetonicum* sequence SEQ ID NO: 21 <223>*Clostridium saccharoperbutylacetonicum* sequence with deletion

The invention claimed is:

1. A process for producing a mutation in an Intended Mutagenesis Region (IMR) within a bacterial genome, wherein the bacteria are of the class Clostridia, wherein the bacteria comprise a CRISPR/Cas system, and wherein the IMR comprises a CRISPR PAM/Protospacer which is capable of being recognised by the bacteria's CRISPR/Cas systems, the process comprising the steps:
   (a) transforming a population of said bacteria with a Recombination Vector, wherein the Recombination Vector comprises a Recombination Element, wherein the Recombination Element comprises:
      (i) a Substitution Element, wherein the Substitution Element comprises the mutation, and
      (ii) Homology Arms which flank the Substitution Element, wherein the Homology Arms are capable of promoting the replacement of all or part of the IMR in the bacterial genome with an element which comprises the Substitution Element,
   wherein the Recombination Element does not comprise a CRISPR PAM/Protospacer which is capable of being recognised by a crRNA which recognises the CRISPR/PAM Protospacer in the IMR;
   (b) culturing the population of bacteria under conditions wherein, in one or more bacteria within the population, all or part of the IMR in the genomes of those bacteria is replaced by an element which comprises the Substitution Element and whereby the CRISPR PAM/Protospacer is removed from the IMR in the genomes of those bacteria or is rendered incapable of being recognised by a crRNA which recognises the CRISPR/PAM Protospacer in the IMR;
   (c) transforming the population of bacteria with a Killing Vector which is capable of directing production of a crRNA which targets the CRISPR PAM/Protospacer in the IMR of any bacteria in the population from which the CRISPR PAM/Protospacer has not been removed or rendered incapable of being recognised by the crRNA, thereby promoting the CAS endonuclease-induced cleavage of those CRISPR PAM/Protospacers in the genomic DNA which are recognised by the crRNA and the subsequent death of those bacteria; and
   (d) selecting or isolating one or more bacteria from the population whose genomes comprise the Substitution Element comprising the mutation.

2. A process as claimed in claim 1, wherein prior to step (c), one or more transformed bacteria are isolated and sub-cultured further to produce one or more further populations of bacteria which are then transformed with the Killing Vector.

3. A process as claimed in claim 1, wherein the PAM/Protospacer in the IMR is present within a region of DNA which corresponds in the Recombination Element to:
   (i) the Substitution Element;
   (ii) the overlap between the upstream Homology Arm and the Substitution Element;
   (iii) the overlap between the downstream Homology Arm and the Substitution Element;
   (iv) the upstream Homology Arm; or
   (v) the downstream Homology Arm.

4. A process as claimed in claim 3, wherein the PAM/Protospacer in the IMR is present within a region of DNA which corresponds in the Recombination Element to:
   (i) the Substitution Element;
   (ii) the overlap between the upstream Homology Arm and the Substitution Element; or
   (iii) the overlap between the downstream Homology Arm and the Substitution Element.

5. A process as claimed in claim 4, wherein the PAM/Protospacer in the IMR is present within a region of DNA which corresponds to the Substitution Element.

6. A process as claimed in claim 1, wherein the Killing Vector comprises:
   (i) a Cas Leader Element
   (ii) a first Cas Direct Repeat Element
   (iii) a Cas Spacer Element which encodes a crRNA which targets the CRISPR PAM/Protospacer in the IMR; and
   (iv) a second Cas Direct Repeat Element.

7. A process as claimed in claim 1, wherein the mutation is a substitution, deletion or insertion of one or more nucleotides, or a combination of one or more substitution, deletion or insertion.

8. A process as claimed in claim 7, wherein the mutation is in the PAM/Protospacer.

9. A process as claimed in claim 7, wherein the mutation is a SNP.

10. A process as claimed in claim 1, wherein the bacteria have an endogenous CRISPR/Cas system.

11. A process as claimed in claim 1, wherein the bacteria have a Type I CRISPR/Cas system.

12. A process as claimed in claim 1, wherein the bacteria are of the genus *Clostridium*.

13. A process as claimed in claim 12, wherein the bacteria are selected from the group consisting of *C. acetobutylicum, C. arbusti, C. aurantibutyricum, C. beijerinckii, C. cellulovorans, C. cellulolyticum, C. thermocellum, C. thermobutyricum, C. pasteurianum, C. kluyveri, C. novyi, C. saccharobutylicum, C. thermosuccinogenes, C. thermopalmarium, C. saccharolyticum, C. saccharoperbutylacetonicum, C. tyrobutyricum, C. tetanomorphum, C. magnum, C. ljungdahlii, C. autoethanogenum, C. butyricum, C. puniceum, C. diolis, C. homopropionicum* and *C. roseum*.

14. A process for making a mutated bacterium, which comprises producing a mutation in an Intended Mutagenesis Region (IMR) within a bacterial genome of a bacterium by a process as claimed in claim 1.

* * * * *

SEQUENCE LISTING

<160> NUMBER OF SEQ ID NOS: 22

<210> SEQ ID NO 1
<211> LENGTH: 52
<212> TYPE: DNA
<213> ORGANISM: Clostridium saccharoperbutylacetonicum

<400> SEQUENCE: 1
ccacttgctg ctccagcgtt tcctagggga ccatatagat tcatatagat tt        52

```
<210> SEQ ID NO 2
<211> LENGTH: 37
<212> TYPE: DNA
<213> ORGANISM: Clostridium saccharoperbutylacetonicum

<400> SEQUENCE: 2
cttgctgctc cagcgtttcc tagggggacca tatagat                              37

<210> SEQ ID NO 3
<211> LENGTH: 52
<212> TYPE: DNA
<213> ORGANISM: Artificial Sequence
<220> FEATURE:
<223> OTHER INFORMATION: Partial sequence of Recombination Vector with
      Substitution Element

<400> SEQUENCE: 3
ctacttgctg ctccagcgtt tccaagagga ccatatagat tcatatagat tt              52

<210> SEQ ID NO 4
<211> LENGTH: 120
<212> TYPE: DNA
<213> ORGANISM: Clostridium saccharoperbutylacetonicum

<400> SEQUENCE: 4
aggttgatta ttttatgtta gaaagtgaag tatctaaaca aattacaact ccacttgctg      60
ctccagcgtt tcctagggga ccatatagat ttcataatag agaatatcta aacattattt    120

<210> SEQ ID NO 5
<211> LENGTH: 84
<212> TYPE: DNA
<213> ORGANISM: Artificial Sequence
<220> FEATURE:
<223> OTHER INFORMATION: Partial sequence of Recombination Vector with
      Substitution Element

<400> SEQUENCE: 5
aggttgatta ttttatgctt gctgctccag cgtttccaag aggaccatat agatttcata      60
atagagaata tctaaacatt attt                                            84

<210> SEQ ID NO 6
<211> LENGTH: 30
<212> TYPE: DNA
<213> ORGANISM: Clostridium saccharoperbutylacetonicum

<400> SEQUENCE: 6
cttttaatat atccatattg gaatgtaaat                                      30

<210> SEQ ID NO 7
<211> LENGTH: 29
<212> TYPE: DNA
<213> ORGANISM: Clostridium saccharoperbutylacetonicum

<400> SEQUENCE: 7
gttttatatt aactatgagg aatgtaaat                                       29

<210> SEQ ID NO 8
<211> LENGTH: 29
<212> TYPE: DNA
<213> ORGANISM: Clostridium sp. DLVIII

<400> SEQUENCE: 8
gttttatatt aactatgagg aatgtaaat                                       29
```

<210> SEQ ID NO 9
<211> LENGTH: 28
<212> TYPE: DNA
<213> ORGANISM: Clostridium saccharobutylicum

<400> SEQUENCE: 9
gttttatctt aactagagga atgtaaat                                28

<210> SEQ ID NO 10
<211> LENGTH: 30
<212> TYPE: DNA
<213> ORGANISM: Clostridium tyrobutyricum

<400> SEQUENCE: 10
gttgaacctt aacatgagat gtatttaaat                              30

<210> SEQ ID NO 11
<211> LENGTH: 30
<212> TYPE: DNA
<213> ORGANISM: Clostridium tyrobutyricum

<400> SEQUENCE: 11
attgaacctt aacatgagat gtatttaaat                              30

<210> SEQ ID NO 12
<211> LENGTH: 30
<212> TYPE: DNA
<213> ORGANISM: Clostridium saccharobutylicum

<400> SEQUENCE: 12
gattaacatt aacatgagat gtatttaaat                              30

<210> SEQ ID NO 13
<211> LENGTH: 30
<212> TYPE: DNA
<213> ORGANISM: Clostridium saccharobutylicum

<400> SEQUENCE: 13
gttgaagatt aacattatat gttttgaaat                              30

<210> SEQ ID NO 14
<211> LENGTH: 30
<212> TYPE: DNA
<213> ORGANISM: Clostridium saccharobutylicum

<400> SEQUENCE: 14
gttgaagatt aacattatat gttttgaaat                              30

<210> SEQ ID NO 15
<211> LENGTH: 30
<212> TYPE: DNA
<213> ORGANISM: Clostridium pasteurianum

<400> SEQUENCE: 15
gttgaacctt aacataggat gtatttaaat                              30

<210> SEQ ID NO 16
<211> LENGTH: 30
<212> TYPE: DNA
<213> ORGANISM: Clostridium autoethanogenum

<400> SEQUENCE: 16
gttgaacctc aacatgagat gtatttaaat                              30

<210> SEQ ID NO 17
<211> LENGTH: 80
<212> TYPE: DNA
<213> ORGANISM: Clostridium saccharoperbutylacetonicum

<400> SEQUENCE: 17
tgttagaaag tgaagtatct aaacaaatta caactccact tgctgctcca gcgtttccta    60
ggggaccata tagatttcat                                                80

<210> SEQ ID NO 18
<211> LENGTH: 80
<212> TYPE: DNA
<213> ORGANISM: Artificial Sequence
<220> FEATURE:
<223> OTHER INFORMATION: Clostridium saccharoperbutylacetonicum sequence
      with mutated PAM site

<400> SEQUENCE: 18
tgttagaaag tgaagtatct aaacaaatta caactctact tgctgctcca gcgtttccaa    60
gaggaccata tagatttcat                                                80

<210> SEQ ID NO 19
<211> LENGTH: 80
<212> TYPE: DNA
<213> ORGANISM: Artificial Sequence
<220> FEATURE:
<223> OTHER INFORMATION: Mutated Clostridium saccharoperbutylacetonicum
      sequence

<400> SEQUENCE: 19
tgttagaaag tgaagtatct aaacaaatta caactctact tgctgctcca gcgtttccta    60
ggggaccata tagatttcat                                                80

<210> SEQ ID NO 20
<211> LENGTH: 80
<212> TYPE: DNA
<213> ORGANISM: Artificial Sequence
<220> FEATURE:
<223> OTHER INFORMATION: Mutated Clostridium saccharoperbutylacetonicum
      sequence

<400> SEQUENCE: 20
tgttagaaag tgaagtatct aaacaaatta caactctact tgctgctcca gcgtttccaa    60
gaggaccata tagatttcat                                                80

<210> SEQ ID NO 21
<211> LENGTH: 129
<212> TYPE: DNA
<213> ORGANISM: Clostridium saccharoperbutylacetonicum

<400> SEQUENCE: 21
aaaatcttat gtattacaat ctaagaaaag aggttgatta ttttatgtta gaaagtgaag    60
tatctaaaca aattacaact ccacttgctg ctccagcgtt tcctagggga ccatatagat   120
ttcataata                                                           129

<210> SEQ ID NO 22
<211> LENGTH: 93
<212> TYPE: DNA
<213> ORGANISM: Artificial Sequence -continued

```
<220> FEATURE:
<223> OTHER INFORMATION: Clostridium saccharoperbutylacetonicum sequence
      with deletion

<400> SEQUENCE: 22
aaaatcttat gtattacaat ctaagaaaag aggttgatta ttttatgctt gctgctccag      60
cgtttccaag aggaccatat agatttcata ata                                  93
```